(12) United States Patent
Dimitrov et al.

(10) Patent No.: US 10,548,987 B2
(45) Date of Patent: Feb. 4, 2020

(54) ANTIBODY-DRUG CONJUGATES FOR TARGETING CD56-POSITIVE TUMORS

(71) Applicants: The U.S.A., as represented by the Secretary, Department of Health and Human Services, Bethesda, MD (US); The Children's Hospital of Philadelphia, Philadelphia, PA (US)

(72) Inventors: Dimiter S. Dimitrov, Frederick, MD (US); Yang Feng, Frederick, MD (US); John M. Maris, Philadelphia, PA (US); Zhongyu Zhu, Frederick, MD (US); Robyn Tovah Sussman, Philadelphia, PA (US)

(73) Assignees: The United States of America, as represented by the Secretary, Department of Health and Human Services, Bethesda, MD (US); The Children's Hospital of Philadelphia, Philadelphia, PA (US)

( * ) Notice: Subject to any disclaimer, the term of this patent is extended or adjusted under 35 U.S.C. 154(b) by 88 days.

(21) Appl. No.: 15/747,620

(22) PCT Filed: Jul. 29, 2016

(86) PCT No.: PCT/US2016/044777
§ 371 (c)(1),
(2) Date: Jan. 25, 2018

(87) PCT Pub. No.: WO2017/023780
PCT Pub. Date: Feb. 9, 2017

(65) Prior Publication Data
US 2018/0214568 A1   Aug. 2, 2018

Related U.S. Application Data

(60) Provisional application No. 62/199,707, filed on Jul. 31, 2015.

(51) Int. Cl.
| | | |
|---|---|---|
| *A61K 39/00* | (2006.01) | |
| *C07K 16/00* | (2006.01) | |
| *A61K 47/68* | (2017.01) | |
| *C07K 16/28* | (2006.01) | |
| *A61P 35/00* | (2006.01) | |
| *C07K 16/30* | (2006.01) | |

(52) U.S. Cl.
CPC ...... *A61K 47/6803* (2017.08); *A61K 47/6851* (2017.08); *A61P 35/00* (2018.01); *C07K 16/2803* (2013.01); *C07K 16/30* (2013.01); *A61K 2039/507* (2013.01); *C07K 2317/21* (2013.01); *C07K 2317/732* (2013.01)

(58) Field of Classification Search
None
See application file for complete search history.

(56) References Cited

U.S. PATENT DOCUMENTS

| | | | |
|---|---|---|---|
| 7,973,140 B2 | 7/2011 | Green et al. | |
| 8,101,724 B2 | 1/2012 | MacDonald et al. | |
| 8,834,880 B2 | 9/2014 | Green et al. | |
| 2011/0177064 A1 | 7/2011 | Whiteman et al. | |
| 2011/0245108 A1 | 10/2011 | Crea et al. | |
| 2012/0269827 A1 | 10/2012 | Whiteman et al. | |

FOREIGN PATENT DOCUMENTS

WO   WO 2012/138537   10/2012

OTHER PUBLICATIONS

Whiteman et al (Landes Bioscience publication mAbs 6:2 556-566, 2014) (Year: 2014).*
Feng et al., "Differential Killing of CD56-Expressing Cells by Drug-Conjugated Human Antibodies Targeting Membrane-Distal and Membrane-Proximal Non-Overlapping Epitopes," *mAbs*, vol. 8:799-810, 2016.
Gerratana, "Biosynthesis, Synthesis and Biological Activities of Pyrrolobenzodiazepines," *Med. Res. Rev.*, vol. 32:254-293, 2012.
Wachowiak et al., "Universal Expression of Cell Adhesion Molecule NCAM in Neuroblastoma in Contrast to L1: Implications for Different Roles in Tumor Biology of Neuroblastoma?" *Pediatr. Surg. Int.*, vol. 24:1361-1364, 2008.
Whiteman et al., "Lorvotuzumab Mertansine, a CD56-Targeting Antibody-Drug Conjugate with Potent Antitumor Activity Against Small Cell Lung Cancer in Human Xenograft Models," *mAbs*, vol. 6:556-566, 2014.

\* cited by examiner

*Primary Examiner* — Lei Yao
(74) *Attorney, Agent, or Firm* — Klarquist Sparkman, LLP

(57) ABSTRACT

The identification and characterization of two fully human CD56-specific monoclonal antibodies targeting spatially separated epitopes proximal and distal to the plasma membrane is described. Also described are antibody-drug conjugates (ADCs) of the identified antibodies and their use for targeting CD56-expressing tumor cells.

16 Claims, 24 Drawing Sheets
Specification includes a Sequence Listing.

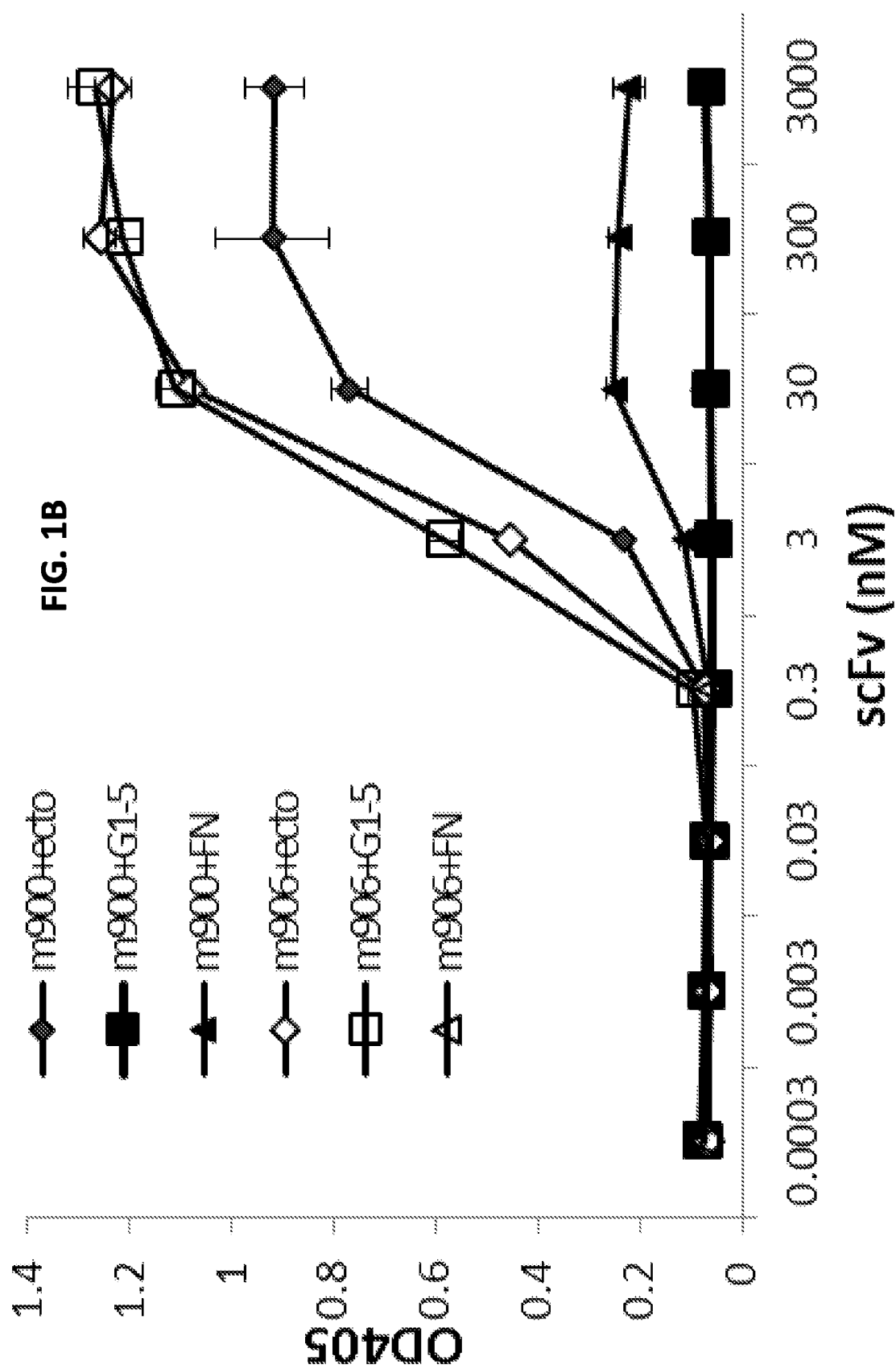

Affinity of m900 an dm906 to CD56 ecto domain:

| Fab | $K_D$ (M) |
|---|---|
| m906 | $4.490 \times 10^{-9}$ |
| m900 | $2.909 \times 10^{-9}$ | m900 and m906 bound to mouse CD56

FIG. 3A
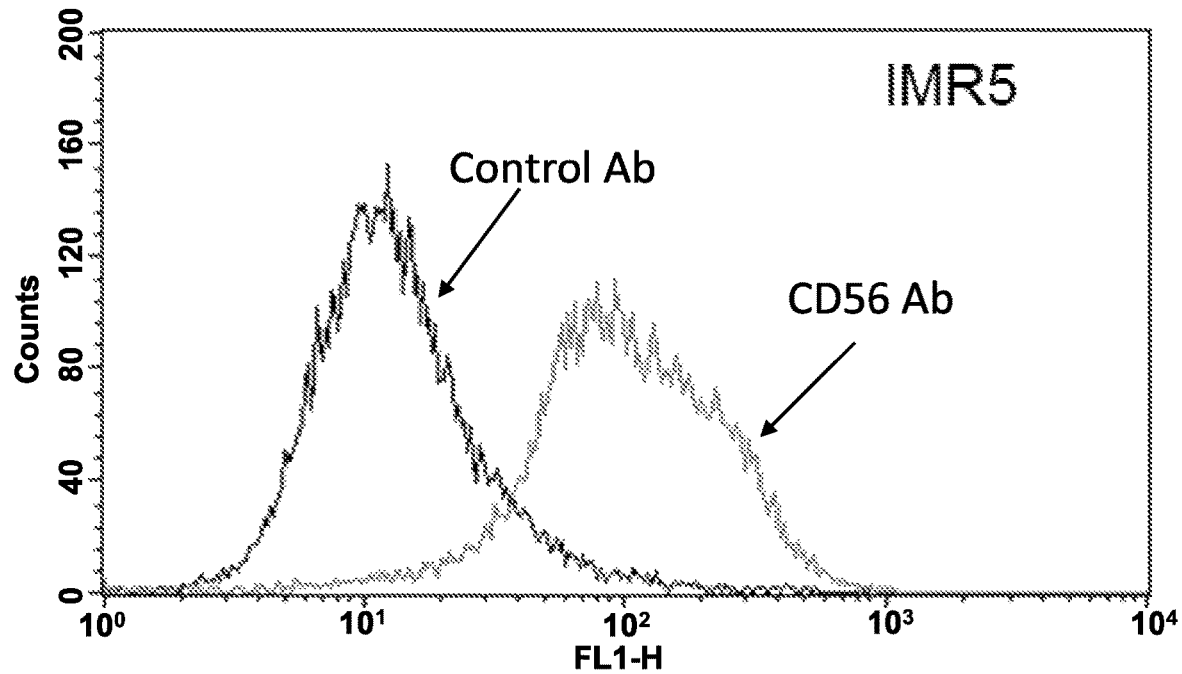
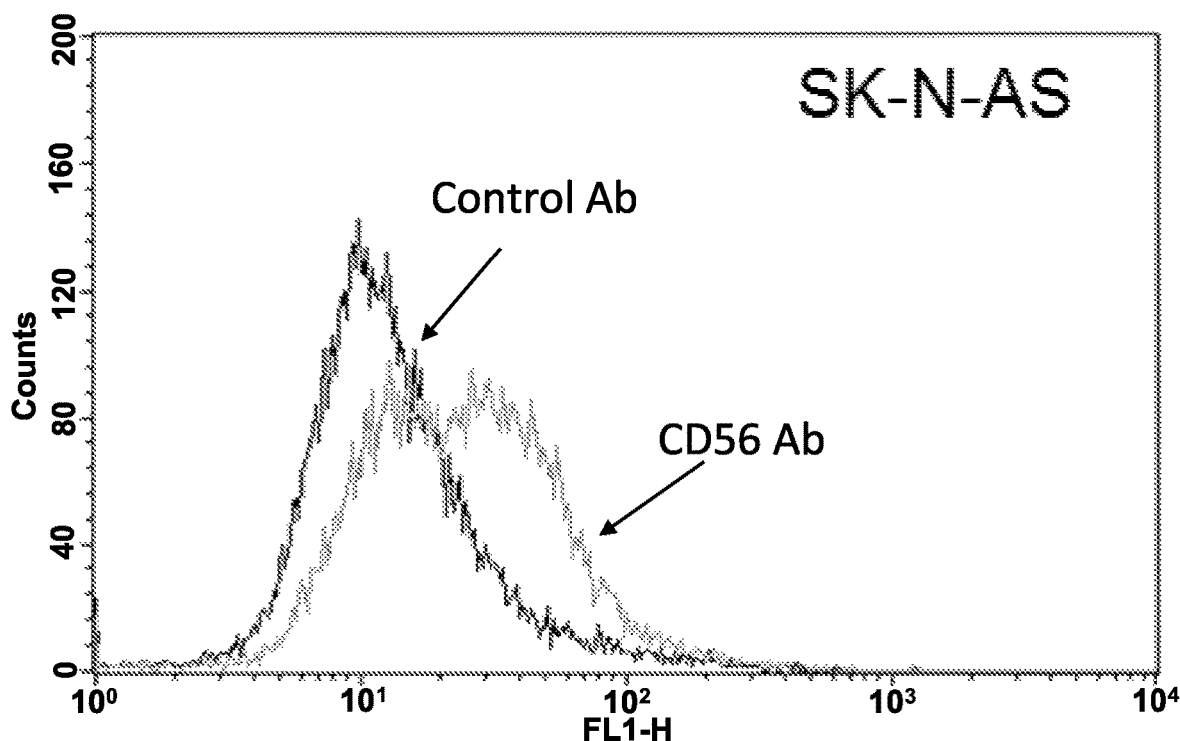

FIG. 3B
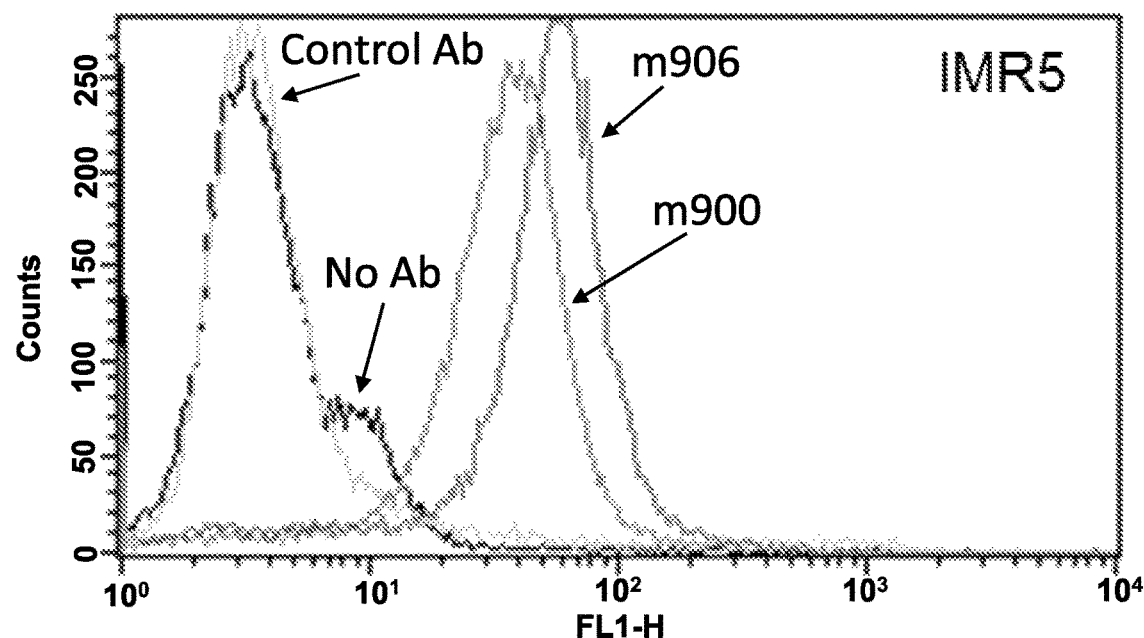
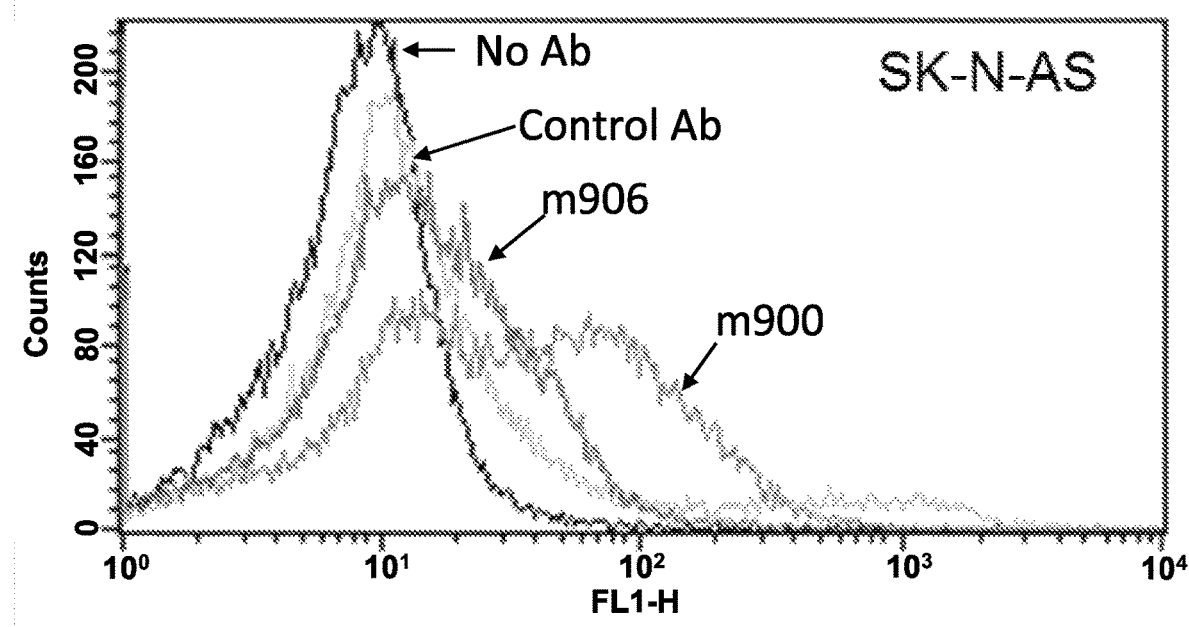

FIG. 4A

| Cell Lines | By m900 | By m906 | By control Ab |
|---|---|---|---|
| IMR5 | 0 | 69% | 0 |
| SK-N-AS | 0 | 47% | 0 |

FIG. 4B
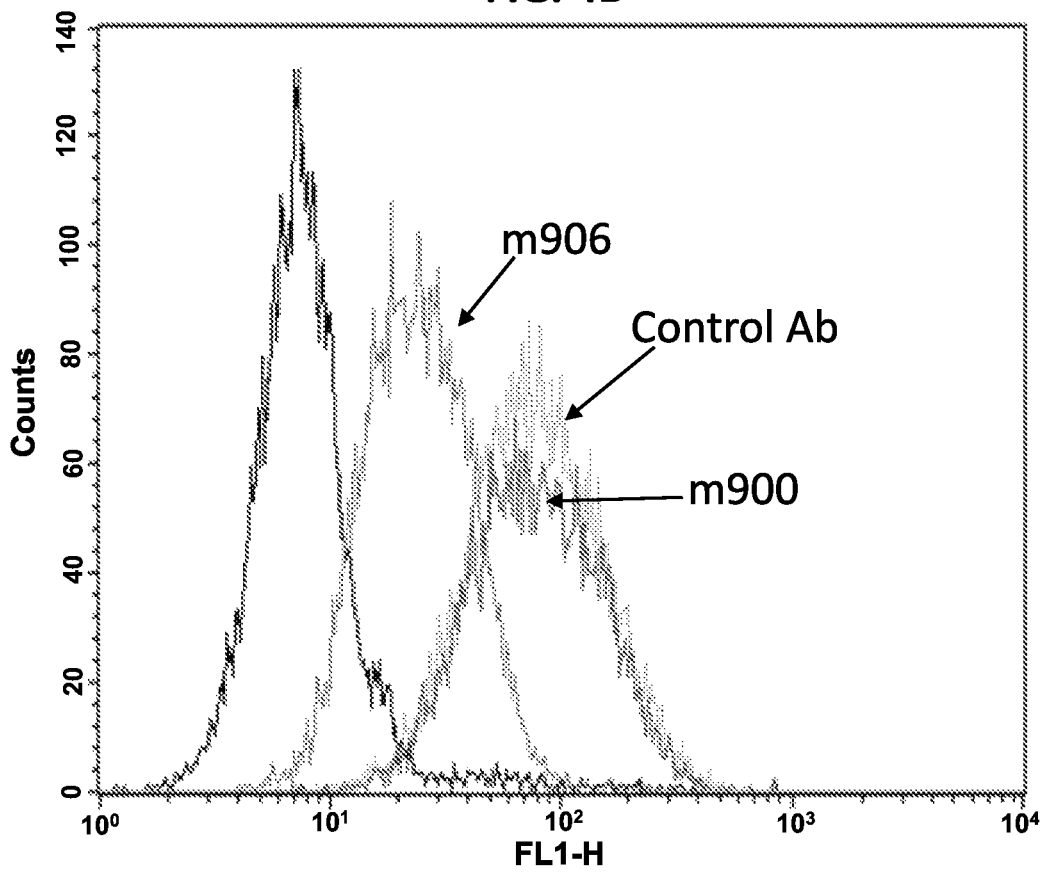
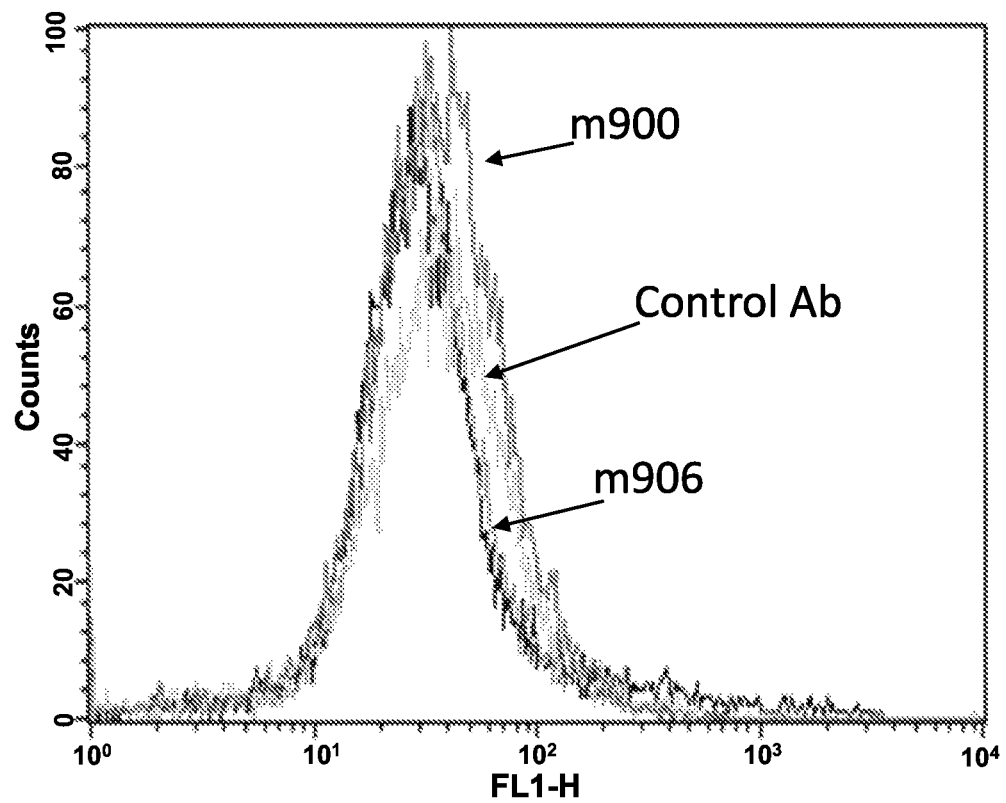

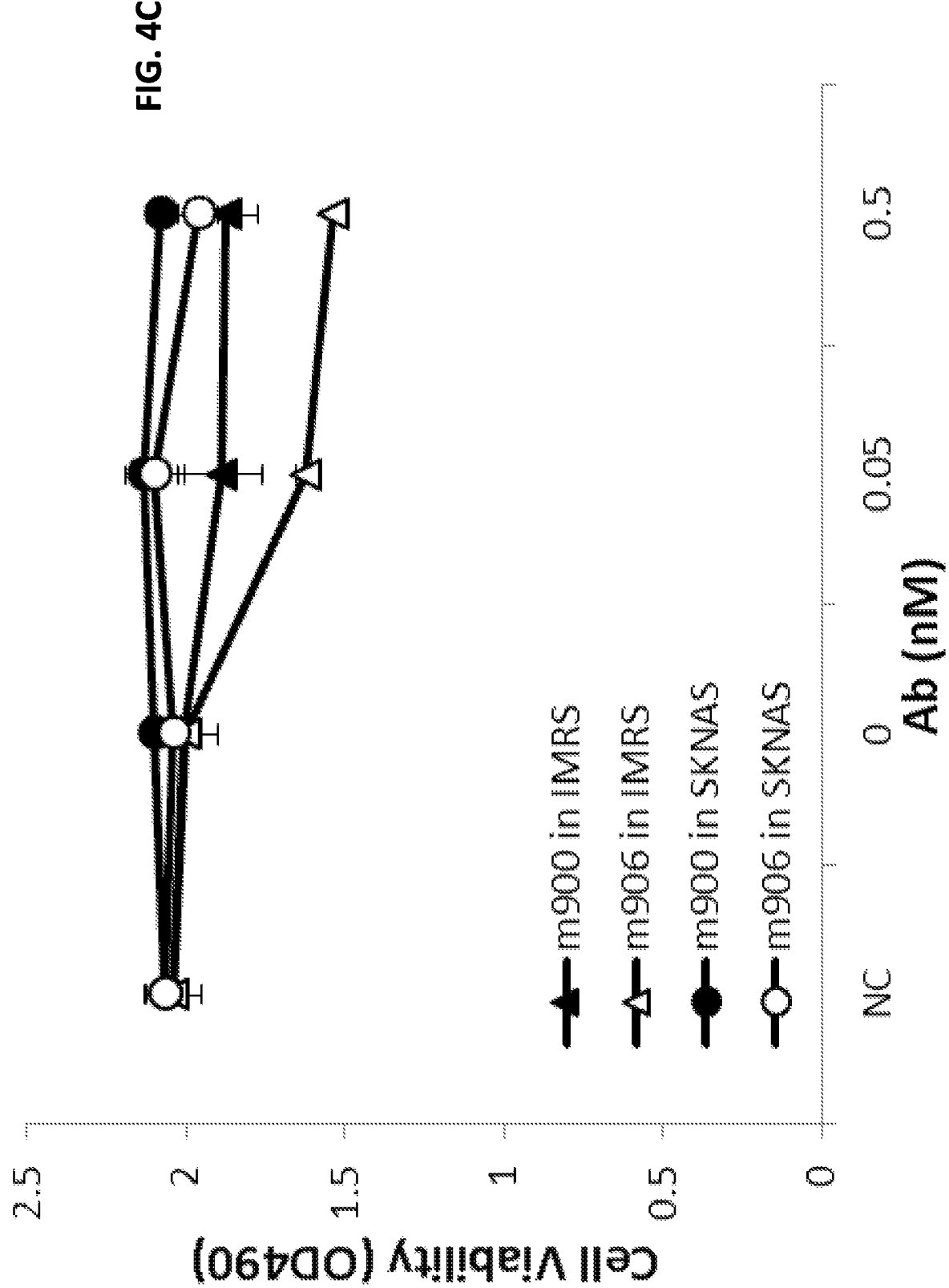

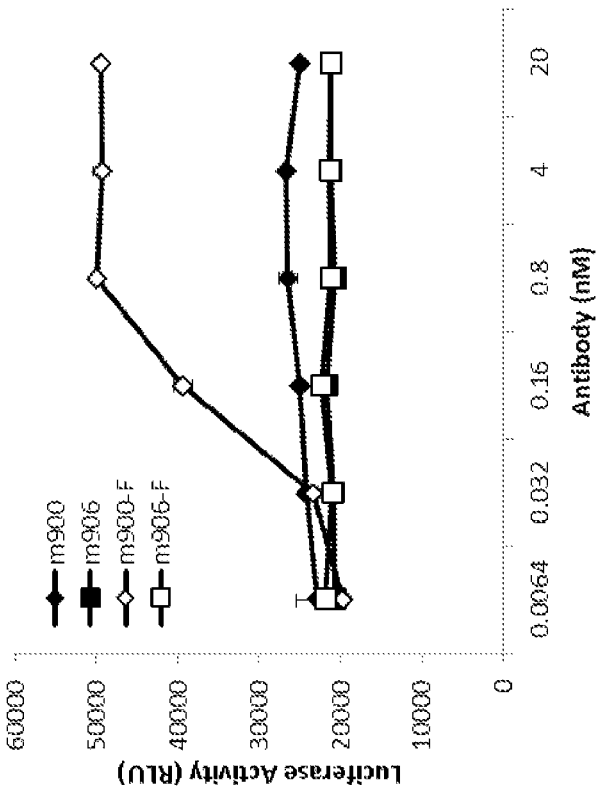
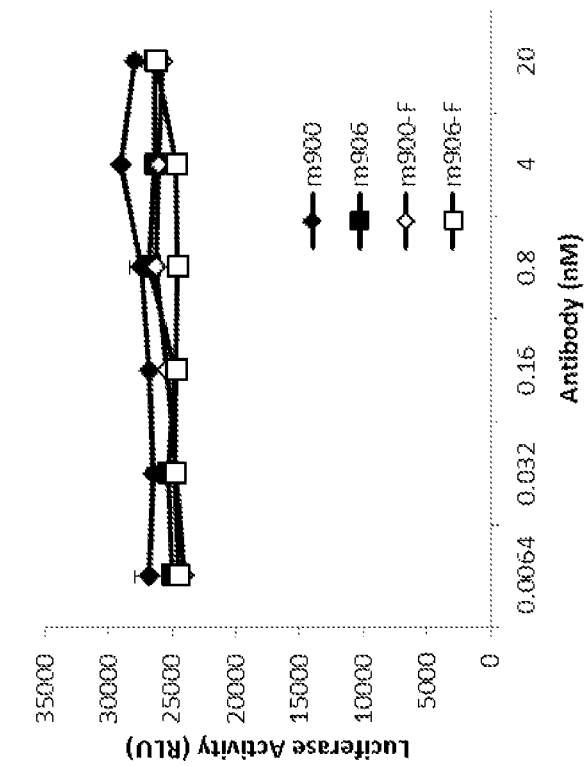
FIG. 6

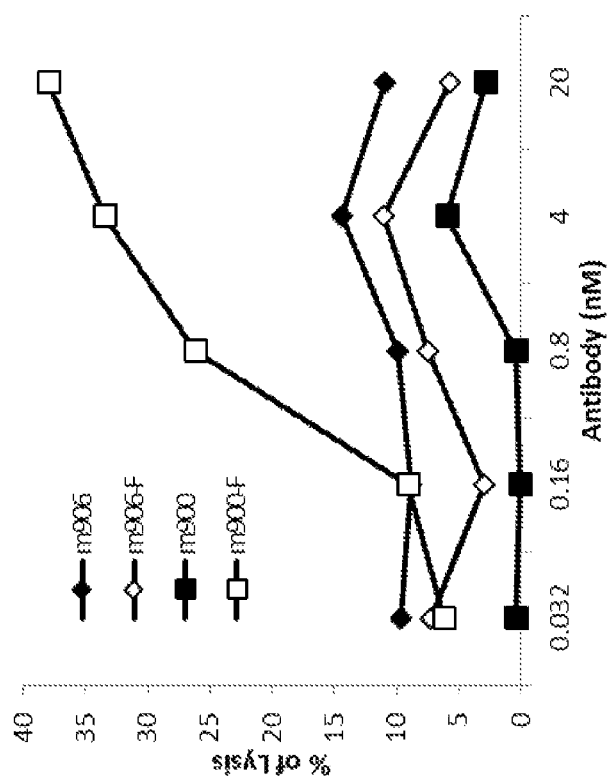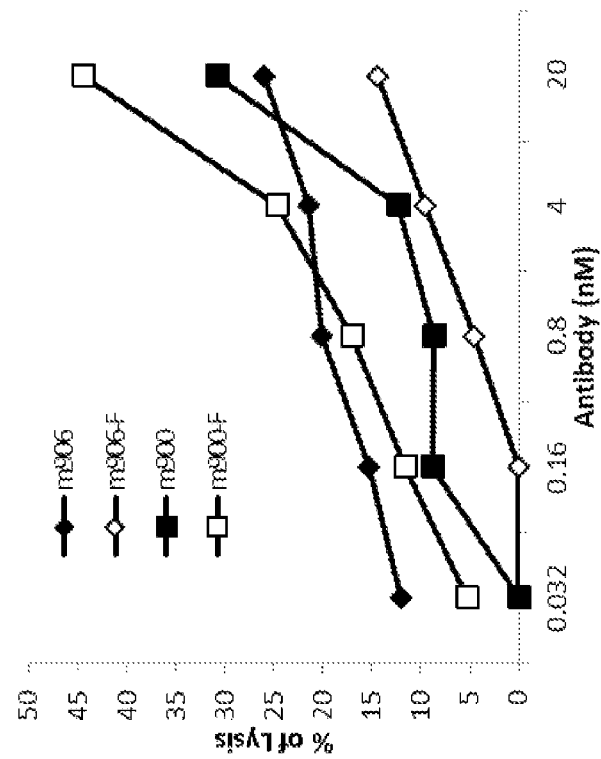
FIG. 7

FIG. 8 Conjugation of Antibodies with an Active Azide-Galactose (C2-Azide-Gal) Using A Full length Mutant Enzyme

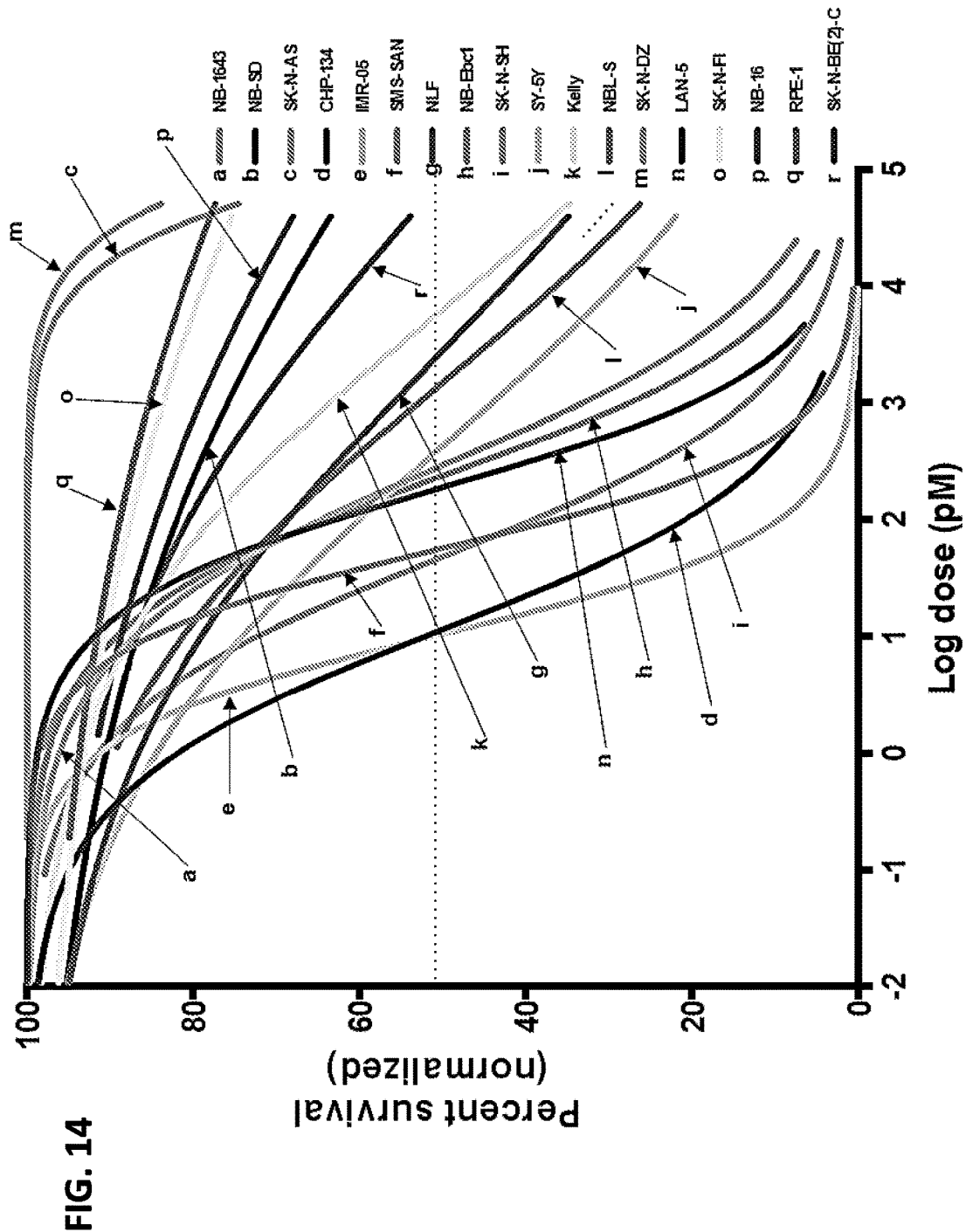

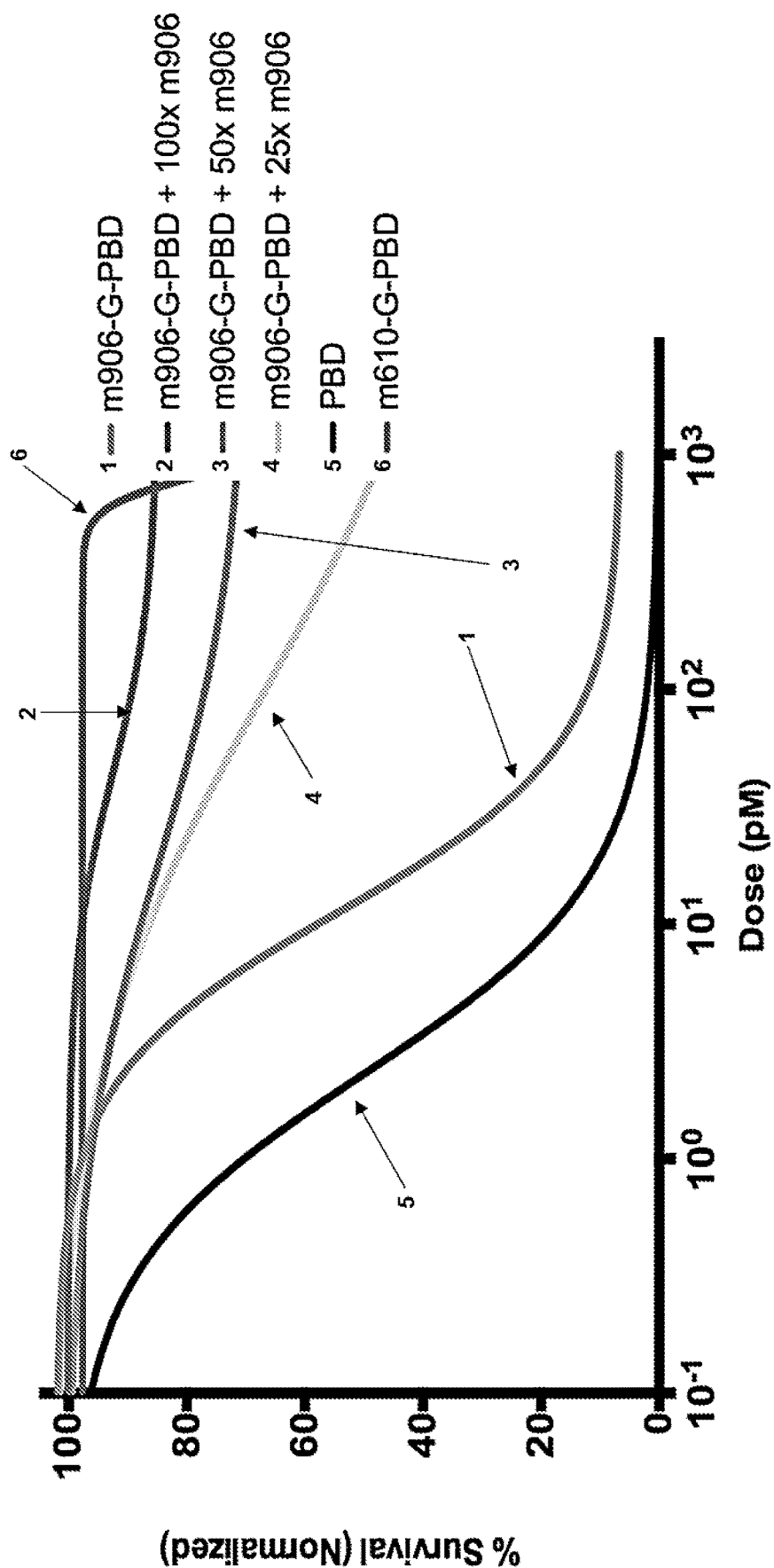

SEQUENCE LISTING

```
<160> NUMBER OF SEQ ID NOS: 8

<210> SEQ ID NO 1
<211> LENGTH: 372
<212> TYPE: DNA
<213> ORGANISM: Artificial Sequence
<220> FEATURE:
```

<223> OTHER INFORMATION: Synthetic polynucleotide

<400> SEQUENCE: 1

```
caggtacagc tgcagcagtc aggtccagga ctggtgaagc cctcgcagac cctctcactc      60
acctgtgcca tctccgggga cagtgtctct agcaacagtg ctgcttggaa ctggatcagg     120
cagtccccat cgagaggcct tgagtggctg ggaaggacat actacaggtc caagtggtat     180
aatgattatg cagtatctgt gaaaagtcga ataaccatca cccagacac atccaagaac      240
cagttctccc tgcagctgaa ctctgtgact cccgaggaca cggctgtgta ttactgtgca     300
agagagaaca tagcagcttg gacctgggct tttgatatct ggggccaagg gacaatggtc     360
accgtctctt ca                                                        372
```

<210> SEQ ID NO 2
<211> LENGTH: 124
<212> TYPE: PRT
<213> ORGANISM: Artificial Sequence
<220> FEATURE:
<223> OTHER INFORMATION: Synthetic polypeptide

<400> SEQUENCE: 2

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Asn Ile Ala Ala Trp Thr Trp Ala Phe Asp
            100                 105                 110

Ile Trp Gly Gln Gly Thr Met Val Thr Val Ser Ser
        115                 120
```

<210> SEQ ID NO 3
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 3

```
gaaattgtgt tgacgcagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cgtgcaggct     240
gaagatgtgg gggtttatta ctgtcagcaa tatcatggta ctccgacgtt cggccaaggg     300
accaaggtgg aaatcaaacg a                                              321
```

<210> SEQ ID NO 4
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 4

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Val Gln Ala
65                  70                  75                  80

Glu Asp Val Gly Val Tyr Tyr Cys Gln Gln Tyr His Gly Thr Pro Thr
                85                  90                  95

Phe Gly Gln Gly Thr Lys Val Glu Ile Lys Arg Gly Gln Ala Gly
            100                 105                 110

<210> SEQ ID NO 6
<211> LENGTH: 363
<212> TYPE: DNA
<213> ORGANISM: Artificial Sequence
<220> FEATURE:
<223> OTHER INFORMATION: Synthetic polynucleotide

<400> SEQUENCE: 5
gaggtgcagc tggtgcagtc tgggctgag gtgaagaagc ctgggtcctc ggtgaaggtc      60
tcctgcaagg cttctggagg caccttcacc ggctactata tgcactgggt gcgacaggcc    120
cctggacaag gcttgagtg gatgggatgg atcaaccta acagtggtgg cacaaactat     180
gcacagaagt ttcagggcag ggtcaccatg accagggaca cgtccatcag cacagcctac    240
atggagctga gcaggctgag atctgacgac acggccgtgt attactgtgc gagagatttg    300
agtagtggtt attccggtta ctttgactac tggggccagg gaaccctggt caccgtctcc    360
tca                                                                  363

<210> SEQ ID NO 6
<211> LENGTH: 121
<212> TYPE: PRT
<213> ORGANISM: Artificial Sequence
<220> FEATURE:
<223> OTHER INFORMATION: Synthetic polypeptide

<400> SEQUENCE: 6

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Leu Ser Ser Gly Tyr Ser Gly Tyr Phe Asp Tyr Trp Gly

```
                     100                 105                 110
Gln Gly Thr Leu Val Thr Val Ser Ser
            115                 120

<210> SEQ ID NO 7
<211> LENGTH: 339
<212> TYPE: DNA
<213> ORGANISM: Artificial Sequence
<220> FEATURE:
<223> OTHER INFORMATION: Synthetic polynucleotide

<400> SEQUENCE: 7
gatgttgtga tgactcagtc tccactctcc ctgcccgtca cccctggaga gccggcctcc      60
atctcctgca ggtctagtca gagcctccta catagtaatg gatacaactt tttggattgg    120
tacctgcaga agccagggca gtctccacag ctcctgatct atttgggttc taatcgggcc    180
tccggggtcc ctgacaggtt cagtggcagt ggatcaggca cagactttac actgaaaatc    240
agcagagtgg aggctgacga tgttggggtt tattactgca tgcaatctct gcaaactccg    300
tggacgttcg gccacgggac caaggtggaa atcaaacga                           339

<210> SEQ ID NO 8
<211> LENGTH: 113
<212> TYPE: PRT
<213> ORGANISM: Artificial Sequence
<220> FEATURE:
<223> OTHER INFORMATION: Synthetic polypeptide

<400> SEQUENCE: 8

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Phe Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Asp Val Gly Val Tyr Tyr Cys Met Gln Ser
                85                  90                  95

Leu Gln Thr Pro Trp Thr Phe Gly His Gly Thr Lys Val Glu Ile Lys
            100                 105                 110

Arg
```

ANTIBODY-DRUG CONJUGATES FOR TARGETING CD56-POSITIVE TUMORS

CROSS REFERENCE TO RELATED APPLICATIONS

This application is the U.S. National Stage of International Application No. PCT/2016/044777, filed Jul. 29, 2016, published in English under PCT Article 21(2), which claims the benefit of U.S. Provisional Application No. 62/199,707, filed Jul. 31, 2015, which is herein incorporated by reference in its entirety.

FIELD

This disclosure concerns antibody-drug conjugates (ADCs) that specifically target CD56-expressing tumors, and their use for treating cancer.

BACKGROUND

CD56, also known as neural cell adhesion molecule 1 (NCAM1), is a type I membrane glycoprotein involved in cell-cell and cell-matrix adhesion. Its extracellular domain has five IgG-like domains at the N-terminus and two fibronectin type III domains in the membrane-proximal region. It has been reported that the function of CD56 is important for cell migration and tumor metastasis. The two domains are thought to have different functional roles, with the IgG-like domains involved in homophilic interactions with other CD56 molecules, either on the same cell or a neighboring cell (Jensen and Berthold, *Cancer Lett* 258(1): 9-21, 2007). The fibronectin type III domains are believed to mediate signaling to downstream proteins. CD56 is overexpressed in nearly all neuroblastomas (Wachowiak et al., *Pediatr Surg Int* 24(12):1361-1364, 2008), 98% of small cell lung cancers (Zheng and Maleki, *Acta Cytol* 57(3):281-290, 2013; Whiteman, et al., *MAbs* 6(2):556-566, 2014) and 78% of multiple myelomas (Lutz and Whiteman, *MAbs* 1(6):548-551, 2009). In addition, some ovarian cancers also exhibit elevated CD56 levels (Ohishi et al., *Gynecol Oncol* 107(1): 30-38, 2007).

SUMMARY

Human monoclonal antibodies that bind CD56, and antibody-drug conjugates (ADCs) comprising the CD56-specific antibodies are disclosed. Also disclosed are compositions comprising the monoclonal antibodies and/or ADCs. The disclosed antibodies, ADCs and compositions can be used, for example, to treat a CD56-positive cancer in a subject.

Provided herein are ADCs comprising a drug conjugated to a CD56-specific monoclonal antibody, or antigen-binding fragment thereof, wherein the antibody or antigen-binding fragment comprises a variable heavy (VH) and a variable light (VL) domain. In some embodiments, the amino acid sequence of the VH domain and/or the amino acid sequence of the VL domain of the antibody includes at least one (such as all three) complementarity determining regions (CDRs) of the VH domain and/or the VL domain of the m906 or m900 antibody disclosed herein. The drug can be, for example, a cytotoxic agent, such as an interstrand crosslinking agent, an anti-mitotic agent or an anti-microtubule agent.

Also provided herein are compositions comprising the disclosed ADCs and a pharmaceutically acceptable carrier.

Further provided are compositions comprising (1) an ADC in which the antibody comprises a first CD56-specific monoclonal antibody or antigen-binding fragment thereof that comprises the CDR sequences of the m906 antibody and (2) a second (non-conjugated) CD56-specific monoclonal antibody or antigen-binding fragment thereof, wherein the second CD56-specific monoclonal antibody or antigen-binding fragment comprises the CDR sequences of antibody m900. In some embodiments, the compositions further include a pharmaceutically acceptable carrier.

Also provided are methods of treating a subject having a CD56-positive cancer, and methods of inhibiting tumor growth or metastasis of a CD56-positive cancer in a subject. In some embodiments, the methods include selecting a subject with a CD56-positive cancer and administering to the subject a therapeutically effective amount of an ADC or composition disclosed herein.

The foregoing and other objects, features, and advantages of the invention will become more apparent from the following detailed description, which proceeds with reference to the accompanying figures.

BRIEF DESCRIPTION OF THE DRAWINGS

FIG. 1B is a graph showing binding of m900 and m906 scFv to different regions of the CD56 ectodomain as determined by enzyme-linked immunosorbent assay (ELISA); ecto, whole ectodomain; G1-5, N-terminal IgG-like domains; FN, fibronectin type III domains.

FIG. 3A is a pair of graphs showing CD56 surface levels in two neuroblastoma cell lines (IMR5—top; SK-N-AS—bottom) measured with a CD56-specific mouse monoclonal antibody. A mouse IgG was used as a negative control. Primary antibodies were used at a concentration of 50 nM. Goat anti-mouse Fc specific polyclonal antibody with fluorescein isothiocyanate (FITC) was use for detection of signal by fluorescence activated cell sorting (FACS).

FIG. 3B is a pair of graphs showing m900 and m906 bound to CD56 on the surface of two neuroblastoma cell lines (IMR5—top; SK-N-AS—bottom). Shown are the binding of a primary antibody-omitted control (No Ab); an isotype control primary antibody (Control Ab); m906; and m900. All primary antibodies were used at a concentration of 50 nM, and goat anti-human Fc specific antibody with FITC was used for signal detection.

FIG. 4A is a table showing the percentage of down-regulation of CD56 surface by overnight incubation of m900, m906 or an isotype control antibody in IMR5 and SK-N-AS cells.

FIG. 4B is a pair of graphs showing CD56 surface levels of two neuroblastoma cell lines (IMR5—top; SK-N-AS—bottom) following overnight incubation of the m906 and m900 antibody. Cells were treated with a control antibody, m900, or m906 and then stained with mouse anti-CD56 antibody.

FIG. 4C is a graph showing antibody-induced internalization of CD56 in NB cells. Binding of m906 induced internalization of the antibody with Fab-ZAP, whereas m900 binding did not induce internalization.

FIG. 6 is a pair of graphs showing defucosylated m900 mediated antibody-dependent cellular cytotoxicity (ADCC) in SK-N-AS cells. The target IMR5 (left) or SK-N-AS (right) cells were incubated with the effector cells Jurakt+ CD16a at a 1:6 ratio for 6 hours with the presence of the test antibody at concentrations from 0.0064 nM to 20 nM. Interaction of antigen bound antibodies with CD16a was reported with the luciferase activities, which were shown as readings on the Y-axis. An isotype control antibody was tested at 20 nM and no detectable ADCC was observed. Each concentration was tested in duplicate.

FIG. 7 is a pair of graphs showing defucosylated m900 mediated ADCC in SK-N-AS cells. Peripheral blood mononuclear cells (PBMCs) isolated from a healthy donor were used as effector cells. The target cells (IMR5—left; SK-N-AS—right) were incubated with effector cells and antibodies for 16 hours at 37° C. Lactose dehydrogenase activities leaked from lysed cells were measured with the addition of fluorogenic substrate. Percentage of lysis at each concentration is shown.

(FIG. 13A) Kelly cells and SKNAS cells were either untreated or treated overnight with 25 nM control IgG, 12.5 nM m906, 25 nM m906 or 50 nM m906 and the remaining cell surface expression of CD56 was detected using anti-CD56 antibody MY31. The results show that untreated and control IgG treated Kelly cells express CD56 on the surface, and this expression is reduced in cells pre-treated with m906. The percent reduction in cell surface expression was calculated using the 50 nM m906 treatment and no treatment groups (1−(m906/no treatment)). SKNAS cells express very little CD56 and showed little difference in CD56 cell surface expression when pre-treated with m906. (FIG. 13B) Other neuroblastoma cell lines were tested as in FIG. 13A, by overnight pre-treatment with 50 nM m906. The percent reduction in CD56 cell surface expression resulting from m906 pre-treatment is indicated in the graph for each cell line. Error bars represent standard error from triplicate experiments. RPE1 is a non-neuroblastoma control-immortalized retinal pigment epithelial cell line.

FIG. 14 is a graph showing the results of an in vitro cell death assay. Seventeen neuroblastoma cell lines were treated with limiting dilutions of m906-PBD for 96 hours. The dose response curves are shown in the graph. IC50 concentrations are in the picomolar range.

FIG. 16 is a graph showing the results of an antibody competition assay. CHP134 cells were treated with limiting dilutions of m906-PBD or free PBD. M906 was used to compete off m906-PBD at 25×, 50× and 100× the m906-PBD dose. M906 was able to prevent cell death in a dose-dependent manner.

(FIG. 17A) Treatment with m906-PBD induced prolonger tumor regression. Error bars represent standard error from 8 mice treated per arm. The 3 mg/kg arm had two mice with no detectable disease for over 150 days post enrollment. (FIG. 17B) Survival is shown in the Kaplan-Meier plot and the significance of the difference between 3 mg/kg m906PBD and m906 or PBS arms is p<0.0001.

SEQUENCE LISTING

Figure 1A:
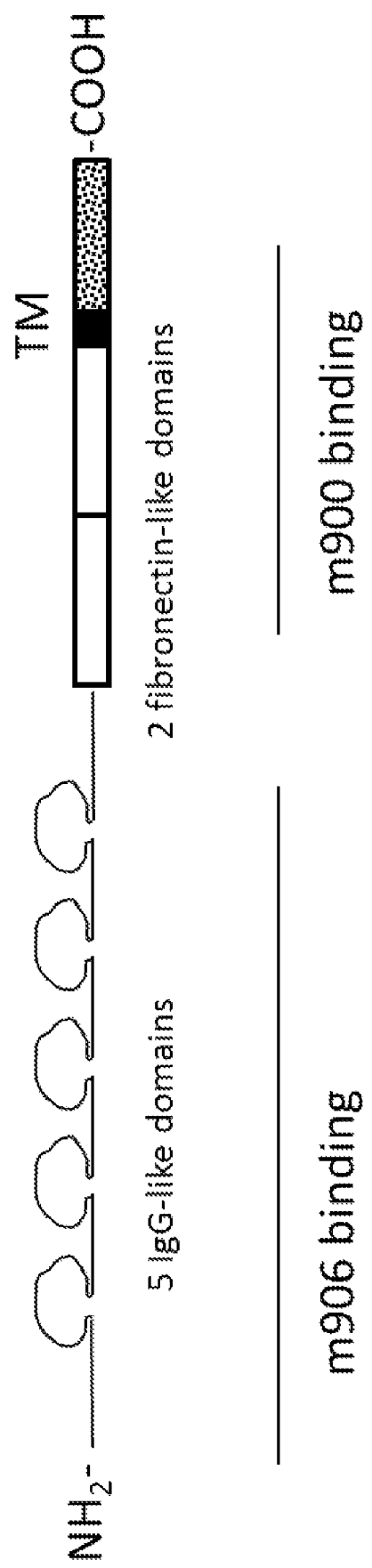
FIG. 1A is a schematic diagram showing the CD56 domain structure and the binding regions of antibodies m900 and m906.
Figure 1C:
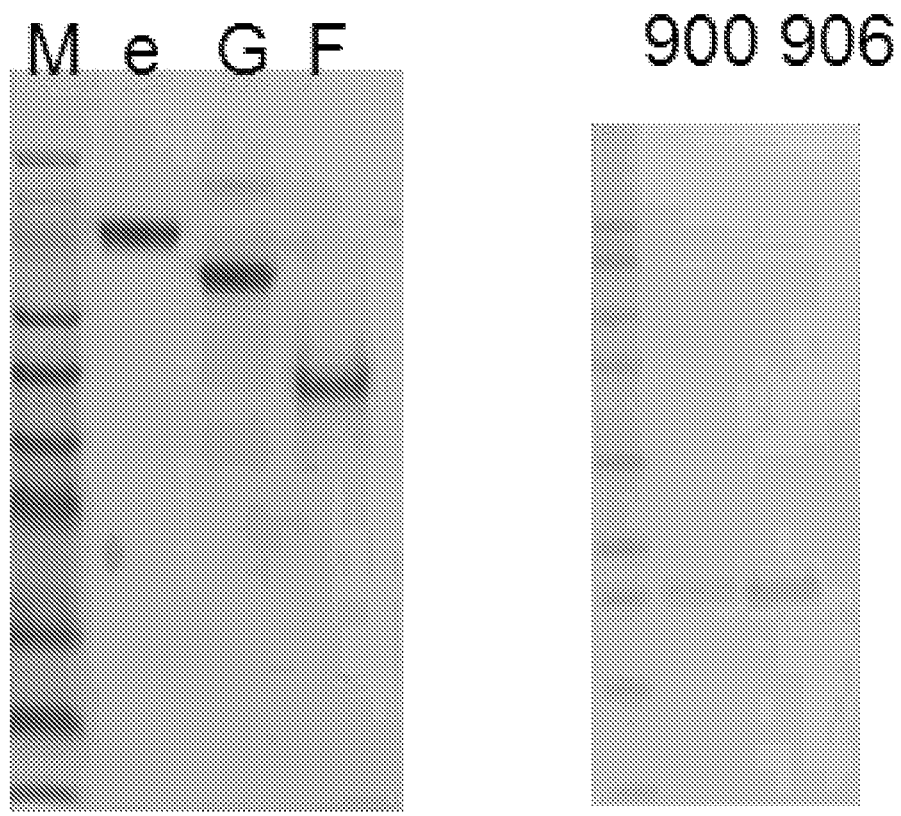
FIG. 1C shows a gel image of purified CD56 recombinant proteins (left). E, whole ectodomain; G, N-terminal IgG-like domains; F, fibronectin type III domains. Fab m900 and m906 are also shown (right).

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Jan. 19, 2018, 7.23 KB, which is incorporated by reference herein. In the accompanying sequence listing:

SEQ ID NO: 1 is the nucleotide sequence of the m900 VH domain.

SEQ ID NO: 2 is the amino acid sequence of the m900 VH domain.

SEQ ID NO: 3 is the nucleotide sequence of the m900 VL domain.

SEQ ID NO: 4 is the amino acid sequence of the m900 VL domain.

SEQ ID NO: 5 is the nucleotide sequence of the m906 VH domain.

SEQ ID NO: 6 is the amino acid sequence of the m906 VH domain.

SEQ ID NO: 7 is the nucleotide sequence of the m906 VL domain.

SEQ ID NO: 8 is the amino acid sequence of the m906 VL domain.

DETAILED DESCRIPTION

I. Abbreviations
ADC antibody-drug conjugate
ADCC antibody-dependent cellular cytotoxicity
CAR chimeric antigen receptor
CDC complement-dependent cytotoxicity
CDR complementarity determining region
ELISA enzyme-linked immunosorbent assay
FACS fluorescence activated cell sorting
FBS fetal bovine serum
FITC fluorescein isothiocyanate
LDH lactate dehydrogenase
NCAM1 neural cell adhesion molecule 1
PBD pyrrolobenzodiazepine
PBMC peripheral blood mononuclear cell
PE *Pseudomonas* exotoxin
scFv single chain variable fragment
VH variable heavy
VL variable light II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Anti-microtubule agent: A drug that interferes with microtubules. Anti-microtubule agents block cell growth by stopping mitosis.

Anti-mitotic agent: A drug or compound that blocks mitosis.

Antibody: A polypeptide ligand comprising at least a light chain and/or heavy chain immunoglobulin variable region which recognizes and binds (such as specifically recognizes and specifically binds) an epitope of an antigen, such as CD56, or a fragment thereof. Immunoglobulin molecules are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antibodies include intact immunoglobulins and the variants and portions (fragments) of antibodies well known in the art, such as single-domain antibodies (e.g. VH domain antibodies), Fab fragments, Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term "antibody" also includes genetically engineered forms such as chimeric antibodies (for example, humanized murine antibodies) and heteroconjugate antibodies (such as bispecific antibodies). See also, *Pierce Catalog and Handbook*, 1994-1995 (Pierce Chemical Co., Rockford, Ill.); Kuby, J., *Immunology*, 3rd Ed., W. H. Freeman & Co., New York, 1997.

Typically, a naturally occurring immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region and a variable region (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The amino acid sequence boundaries of a given CDR can be readily determined using any of a number of well-known schemes, including those described by Kabat et al. (*Sequences of Proteins of Immunological Interest*, U.S. Department of Health and Human Services, 1991; the "Kabat" numbering scheme), Chothia et al. (see Chothia and Lesk, *J Mol Biol* 196:901-917, 1987; Chothia et al., *Nature* 342:877, 1989; and Al-Lazikani et al., (JMB 273,927-948, 1997; the "Chothia" numbering scheme), and the ImMunoGeneTics (IMGT) database (see, Lefranc, *Nucleic Acids Res* 29:207-9, 2001; the "IMGT" numbering scheme). The Kabat and IMGT databases are maintained online. The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are often identified by the chain in which the particular CDR is located. Thus, a $V_H$ CDR3 (or HCDR3) is located in the variable domain of the heavy chain of the antibody in which it is found, whereas a $V_L$ CDR1 (or LCDR1) is the CDR1 from the variable domain of the light chain of the antibody in which it is found. An antibody that binds CD56, for example, will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and/or heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a murine antibody that specifically binds CD56.

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. A "humanized" immunoglobulin is an immunoglobulin including a human framework region and one or more CDRs from a non-human (for example a mouse, rabbit, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

Antibody-drug conjugate (ADC): A molecule that includes an antibody (or antigen-binding fragment of an antibody) conjugated to a drug, such as a cytotoxic agent. ADCs can be used to specifically target a drug to cancer cells through specific binding of the antibody to a tumor antigen expressed on the cell surface. Exemplary drugs for use with ADCs include anti-microtubule agents (such as maytansinoids, auristatin E and auristatin F) and interstrand cross-linking agents (e.g., pyrrolobenzodiazepines; PDBs).

Anti-microtubule agent: A type of drug that blocks cell growth by stopping mitosis. Anti-microtubule agents, also referred to as "anti-mitotic agents," are used to treat cancer.

Binding affinity: Affinity of an antibody for an antigen. In one embodiment, affinity is calculated by a modification of the Scatchard method described by Frankel et al. (*Mol. Immunol.*, 16:101-106, 1979). In another embodiment, binding affinity is measured by an antigen/antibody dissociation rate. In another embodiment, binding affinity is measured by a competition radioimmunoassay. In another embodiment, binding affinity is measured by ELISA. An antibody that "specifically binds" an antigen (such as CD56) is an antibody that binds the antigen with high affinity and does not significantly bind other unrelated antigens.

CD56: A member of the immunoglobulin superfamily involved in cell-to-cell interactions as well as cell-matrix interactions during development and differentiation. CD56 is also known as neural cell adhesion molecule 1 (NCAM1). CD56 is overexpressed in several types of cancer, including neuroblastoma, small cell lung cancer, multiple myeloma, acute myeloid leukemia, Wilms tumor and ovarian cancer.

Chemotherapeutic agent: Any chemical agent with therapeutic usefulness in the treatment of diseases characterized by abnormal cell growth. Such diseases include tumors, neoplasms, and cancer as well as diseases characterized by hyperplastic growth, such as psoriasis. In one embodiment, a chemotherapeutic agent is an agent of use in treating a CD56-positive cancer, such as neuroblastoma, small cell lung cancer, multiple myeloma, acute myeloid leukemia, Wilms tumor or ovarian cancer. In one embodiment, a chemotherapeutic agent is a radioactive compound. One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer, L., Berkery, R. (eds.): *Oncology Pocket Guide to Chemotherapy*, 2nd ed. St. Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993). Combination chemotherapy is the administration of more than one agent to treat cancer. One example is the administration of an antibody (or immunoconjugate or ADC) that binds CD56 used in combination with a radioactive or chemical compound.

Chimeric antigen receptor (CAR): A chimeric molecule that includes an antigen-binding portion (such as a monoclonal antibody or fragment thereof) and a signaling domain, such as a signaling domain from a T cell receptor (e.g. CD3ζ). Typically, CARs are comprised of a binding moiety (e.g. a scFv), a transmembrane domain and an endodomain. The endodomain typically includes a signaling chain having an immunoreceptor tyrosine-based activation motif (ITAM), such as CD3ζ or FcεRIγ. In some instances, the endodomain further includes the intracellular portion of at least one additional co-stimulatory domain, such as CD28 and/or CD137.

Conservative variant: "Conservative" amino acid substitutions are those substitutions that do not substantially affect or decrease the affinity of a protein, such as an antibody to CD56. For example, a monoclonal antibody that specifically binds CD56 can include at most about 1, at most about 2, at most about 5, at most about 10, or at most about 15 conservative substitutions and specifically bind a CD56 polypeptide. The term "conservative variant" also includes the use of a substituted amino acid in place of an unsubstituted parent amino acid, provided that the antibody specifically binds CD56. Non-conservative substitutions are those that reduce an activity or binding to CD56.

Complementarity determining region (CDR): Amino acid sequences which together define the binding affinity and specificity of the natural Fv region of a native Ig binding site. The light and heavy chains of an Ig each have three CDRs, designated LCDR1, LCDR2, LCDR3 and HCDR1, HCDR2 and HCDR3, respectively.

Contacting: Placement in direct physical association; includes both in solid and liquid form.

Cytotoxic agent: Any drug or compound that kills cells.

Degenerate variant: In the context of the present disclosure, a "degenerate variant" refers to a polynucleotide encoding a CD56 polypeptide or an antibody that binds CD56 that includes a sequence that is degenerate as a result of the genetic code. There are 20 natural amino acids, most of which are specified by more than one codon. Therefore, all degenerate nucleotide sequences are included as long as the amino acid sequence of the CD56 polypeptide or antibody that binds CD56 encoded by the nucleotide sequence is unchanged.

Diagnostic: Identifying the presence or nature of a pathologic condition, such as, but not limited to, cancer. Diagnostic methods differ in their sensitivity and specificity. The "sensitivity" of a diagnostic assay is the percentage of diseased individuals who test positive (percent of true positives). The "specificity" of a diagnostic assay is one minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" is the probability of development (e.g., severity) of a pathologic condition, such as cancer or metastasis.

Drug: Any compound used to treat, ameliorate or prevent a disease or condition in a subject. In some embodiments herein, the drug is an anti-cancer agent, for example a cytotoxic agent, such as an anti-mitotic or anti-microtubule agent.

Effector molecule: The portion of an antibody conjugate (or immunoconjugate) that is intended to have a desired effect on a cell to which the conjugate is targeted. Effector molecules are also known as effector moieties (EMs), therapeutic agents, diagnostic agents, or similar terms. Therapeutic agents (or drugs) include such compounds as small molecules, nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides. Alternatively, the effector molecule can be contained within an encapsulation system, such as a liposome or micelle, which is conjugated to the antibody. Encapsulation shields the effector molecule from direct exposure to the circulatory system. Means of preparing liposomes attached to antibodies are well known to those of skill in the art (see, for example, U.S. Pat. No. 4,957,735; and Connor et al., *Pharm Ther* 28:341-365, 1985). Diagnostic agents or moieties include radioisotopes and other detectable labels (e.g., fluorophores, chemiluminescent agents, and enzymes). Radioactive isotopes include $^{35}S$, $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$ and $^{125}I$.

Epitope: An antigenic determinant. These are particular chemical groups or peptide sequences on a molecule that are antigenic, i.e. that elicit a specific immune response. An antibody specifically binds a particular antigenic epitope on a polypeptide, such as CD56.

Framework region: Amino acid sequences interposed between CDRs. Framework regions include variable light and variable heavy framework regions. The framework regions serve to hold the CDRs in an appropriate orientation for antigen binding.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4$^+$ response or a CD8$^+$ response. In another embodiment, the response is a B cell response, and results in the production of antigen-specific antibodies.

Interstrand crosslinking agent: A type of cytotoxic drug capable of binding covalently between two strands of DNA, thereby preventing DNA replication and/or transcription.

Isolated: An "isolated" biological component, such as a nucleic acid, protein (including antibodies) or organelle, has been substantially separated or purified away from other biological components in the environment (such as a cell) in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}S$, $^{11}C$, $^{13}N$, $^{15}O$, $^{18}F$ $^{19}F$, $^{99m}Tc$, $^{131}I$, $^{3}H$, $^{14}C$, $^{15}N$, $^{90}Y$, $^{99}Tc$, $^{111}In$ and $^{125}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Linker: In some cases, a linker is a peptide within an antibody binding fragment (such as an Fv fragment) which serves to indirectly bond the variable heavy chain to the variable light chain. "Linker" can also refer to a peptide serving to link a targeting moiety, such as an antibody, to an effector molecule, such as a cytotoxin or a detectable label.

The terms "conjugating," "joining," "bonding" or "linking" refer to making two polypeptides into one contiguous polypeptide molecule, or to covalently attaching a radionuclide, drug or other molecule to a polypeptide, such as an antibody or antibody fragment. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Mammal: This term includes both human and non-human mammals. Similarly, the term "subject" includes both human and veterinary subjects.

Multiple myeloma: A type of cancer that begins in plasma cells. In this type of cancer, abnormal plasma cells build up in the bone marrow and form tumors in many bones of the body.

Neoplasia, malignancy, cancer or tumor: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant."

Neuroblastoma: A type of cancer that forms from immature nerve cells. It usually beings in the adrenal gland, but may also begin in the abdomen, chest or in nerve tissue near the spine. Neuroblastoma most often occurs in children younger than 5 years of age.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Ovarian cancer: Cancer that forms in tissues of the ovary (one of a pair of female reproductive glands in which the ova, or eggs, are formed). Most ovarian cancers are either ovarian epithelial carcinomas (cancer that begins in the cells on the surface of the ovary) or malignant germ cell tumors (cancer that begins in egg cells).

Pharmaceutical agent: A chemical compound or composition capable of inducing a desired therapeutic or prophylactic effect when properly administered to a subject or a cell.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the antibodies and conjugates disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop, such as a reduction in tumor burden or a decrease in the number of size of metastases. "Ameliorating" refers to the reduction in the number or severity of signs or symptoms of a disease, such as cancer.

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation. Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Pyrrolobenzodiazepine (PBD): A class of sequence-selective DNA minor-groove binding crosslinking agents originally discovered in *Streptomyces* species. PDBs are significantly more potent than systemic chemotherapeutic drugs. The mechanism of action of PBDs is associated with their ability to form an adduct in the minor groove of DNA, thereby interfering with DNA processing. In the context of the present disclosure, PBDs include naturally produced and isolated PBDs, chemically synthesized naturally occurring PBDs, and chemically synthesized non-naturally occurring PBDs. PBDs also include monomeric, dimeric and hybrid PBDs (for a review see Gerratana, *Med Res Rev* 32(2):254-293, 2012).

Recombinant: A recombinant nucleic acid is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques.

Sample (or biological sample): A biological specimen containing genomic DNA, RNA (including mRNA), protein, or combinations thereof, obtained from a subject. Examples include, but are not limited to, peripheral blood, tissue, cells, urine, saliva, tissue biopsy, fine needle aspirate, surgical specimen, and autopsy material. In one example, a sample includes a tumor biopsy.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide or nucleic acid molecule will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a $V_L$ or a $V_H$ of an antibody that specifically binds CD56 or a fragment thereof are typically characterized by possession of at least about 75%, for example at least about 80%, 90%, 95%, 96%, 97%, 98% or 99% sequence identity counted over the full length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Small cell lung cancer: An aggressive cancer that forms in tissues of the lung and can spread to other parts of the body. The cancer cells appear small and oval-shaped.

Small molecule: A molecule, typically with a molecular weight less than about 1000 Daltons, or in some embodiments, less than about 500 Daltons, wherein the molecule is capable of modulating, to some measurable extent, an activity of a target molecule.

Subject: Living multi-cellular vertebrate organisms, a category that includes both human and veterinary subjects, including human and non-human mammals.

Therapeutically effective amount: A quantity of a specific substance sufficient to achieve a desired effect in a subject being treated. For instance, this can be the amount necessary to inhibit or suppress growth of a tumor. In one embodiment, a therapeutically effective amount is the amount necessary to eliminate, reduce the size, or prevent metastasis of a tumor. When administered to a subject, a dosage will generally be used that will achieve target tissue concentrations (for example, in tumors) that has been shown to achieve a desired in vitro effect.

Toxin: An agent that directly or indirectly inhibits the growth of and/or kills cells. Toxins include, for example, *Pseudomonas* exotoxin (PE, such as PE35, PE37, PE38 and PE40), diphtheria toxin (DT), botulinum toxin, abrin, ricin, saporin, restrictocin or gelonin, or modified toxins thereof. For example, PE and DT are highly toxic compounds that typically bring about death through liver toxicity. PE and DT, however, can be modified into a form for use as an immunotoxin by removing the native targeting component of the toxin (such as domain Ia of PE or the B chain of DT) and replacing it with a different targeting moiety, such as an antibody.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Introduction

CD56, also known as NCAM1, is over-expressed in many types of tumors, including neuroblastoma, multiple myeloma, small cell lung cancer, acute myeloid leukemia, Wilms tumor and ovarian cancer. By using phage display, two high-affinity anti-CD56 fully human monoclonal antibodies were identified, referred to herein as m900 and m906. The two antibodies bind to spatially separated non-overlapping epitopes—m900 binds to the membrane proximal fibronectin type III domains, whereas m906 binds to the N terminal IgG-like domains. The studies disclosed herein demonstrated that m906 induced down-regulation and internalization of CD56 in two neuroblastoma cell lines, IMR5 and SK-N-AS. Although m900 did not significantly induce down-regulation and internalization of CD56, the affinity of the two antibodies was about the same (equilibrium dissociation constant 4.5 and 2.9 nM, respectively).

Antibody-drug conjugates (ADCs) made by conjugation of m900 and m906 with a highly toxic pyrrolobenzodiazepine (PBD) dimer exhibited killing activity that correlated with the extent of CD56 internalization. m906 was highly effective at killing IMR5 cells expressing high levels of internalizable CD56 (50% at 5 pM). In contrast, naked (defucosylated) m900, but not m906, was efficient in mediating antibody-dependent cell-mediated cytotoxicity (ADCC), as measured in a reporter gene assay. In a human PBMC-based assay, m900 (both unmodified and defucosylated) was also a more effective killer than m906. The ADCC was not correlated with the level of CD56 expression as SK-N-AS cells that express relatively low CD56 levels were more efficiently killed, especially by the defucosylated m900. These results support the use of m900 antibodies, m906 ADCs, or a combination thereof, for targeting CD56-expressing cancer cells by specifically targeting non-overlapping spatially separated CD56 epitopes with contrasting functions.

IV. Overview of Several Embodiments

Disclosed herein is the identification and characterization of two fully human CD56-specific antibodies targeting spatially separated epitopes proximal or distal to the plasma membrane. The nucleotide and amino acid sequences of the VH and VL domains of the m900 and m906 antibodies are provided below. The amino acid residues of the VL and VH domain CDRs, according to IMGT and Kabat, are provided in a table below each sequence.

m900 VH (SEQ ID NO: 1)
CAGGTACAGCTGCAGCAGTCAGGTCCAGGACTGGTGAAGCCCTCGCAGACC

CTCTCACTCACCTGTGCCATCTCCGGGGACAGTGTCTCTAGCAACAGTGCT

```
GCTTGGAACTGGATCAGGCAGTCCCCATCGAGAGGCCTTGAGTGGCTGGGA

AGGACATACTACAGGTCCAAGTGGTATAATGATTATGCAGTATCTGTGAAA

AGTCGAATAACCATCAACCCAGACACATCCAAGAACCAGTTCTCCCTGCAG

CTGAACTCTGTGACTCCCGAGGACACGGCTGTGTATTACTGTGCAAGAGAG

AACATAGCAGCTTGGACCTGGGCTTTTGATATCTGGGGCCAAGGGACAATG

GTCACCGTCTCTTCA
                                       (SEQ ID NO: 2)
QVQLQQSGPGLVKPSQTLSLTCAISGDSVSSNSAAWNWIRQSPSRGLEWLG

RTYYRSKWYNDYAVSVKSRITINPDTSKNQFSLQLNSVTPEDTAVYYCARE

NIAAWTWAFDIWGQGTMVTVSS
```

Location of the m900 VH Domain CDRs

| Convention: | IMGT | Kabat |
|---|---|---|
| CDR1 | 26-35 | 31-37 |
| CDR2 | 53-61 | 52-69 |
| CDR3 | 100-114 | 102-113 |

```
m900 VL
                                       (SEQ ID NO: 3)
GAAATTGTGTTGACGCAGTCTCCAGCCACCCTGTCTTTGTCTCCAGGGGA

AAGAGCCACCCTCTCCTGCAGGGCCAGTCAGAGTGTTAGCAGCTACTTAG

CCTGGTACCAACAGAAACCTGGCCAGGCTCCCAGGCTCCTCATCTATGAT

GCATCCAACAGGGCCACTGGCATCCCAGCCAGGTTCAGTGGCAGTGGGTC

TGGGACAGACTTCACTCTCACCATCAGCAGCGTGCAGGCTGAAGATGTGG

GGGTTTATTACTGTCAGCAATATCATGGTACTCCGACGTTCGGCCAAGGG

ACCAAGGTGGAAATCAAACGA
                                       (SEQ ID NO: 4)
EIVLTQSPATLSLSPGERATLSCRASQSVSSYLAWYQQKPGQAPRLLIYD

ASNRATGIPARFSGSGSGTDFTLTISSVQAEDVGVYYCQQYHGTPTFGQG

TKVEIKRGQAG
```

Location of the m900 VL Domain CDRs

| Convention: | IMGT | Kabat |
|---|---|---|
| CDR1 | 27-32 | 24-34 |
| CDR2 | 50-52 | 50-56 |
| CDR3 | 89-97 | 89-96 |

```
m906 VH
                                       (SEQ ID NO: 5)
GAGGTGCAGCTGGTGCAGTCTGGGGCTGAGGTGAAGAAGCCTGGGTCC

TCGGTGAAGGTCTCCTGCAAGGCTTCTGGAGGCACCTTCACCGGCTAC

TATATGCACTGGGTGCGACAGGCCCCTGGACAAGGGCTTGAGTGGATG

GGATGGATCAACCCTAACAGTGGTGGCACAAACTATGCACAGAAGTTT

CAGGGCAGGGTCACCATGACCAGGGACACGTCCATCAGCACAGCCTAC

ATGGAGCTGAGCAGGCTGAGATCTGACGACACGGCCGTGTATTACTGT

GCGAGAGATTTGAGTAGTGGTTATTCCGGTTACTTTGACTACTGGGGC

CAGGGAACCCTGGTCACCGTCTCCTCA
                                       (SEQ ID NO: 6)
EVQLVQSGAEVKKPGSSVKVSCKASGGTFTGYYMHWVRQAPGQGLEWM

GWINPNSGGTNYAQKFQGRVTMTRDTSISTAYMELSRLSDDTAVYYC

ARDLSSGYSGYFDYWGQGTLVTVSS
```

Location of the m906 VH Domain CDRs

| Convention: | IMGT | Kabat |
|---|---|---|
| CDR1 | 26-33 | 31-35 |
| CDR2 | 51-59 | 50-66 |
| CDR3 | 97-111 | 99-110 |

```
m906 VL
                                       (SEQ ID NO: 7)
GATGTTGTGATGACTCAGTCTCCACTCTCCCTGCCCGTCACCCCTGGA

GAGCCGGCCTCCATCTCCTGCAGGTCTAGTCAGAGCCTCCTACATAGT

AATGGATACAACTTTTTGGATTGGTACCTGCAGAAGCCAGGGCAGTCT

CCACAGCTCCTGATCTATTTGGGTTCTAATCGGGCCTCCGGGGTCCCT

GACAGGTTCAGTGGCAGTGGATCAGGCACAGACTTTACACTGAAAATC

AGCAGAGTGGAGGCTGACGATGTTGGGGTTTATTACTGCATGCAATCT

CTGCAAACTCCGTGGACGTTCGGCCACGGGACCAAGGTGGAAATCAAA

CGA
                                       (SEQ ID NO: 8)
DVVMTQSPLSLPVTPGEPASISCRSSQSLLHSNGYNFLDWYLQKPGQS

PQLLIYLGSNRASGVPDRFSGSGSGTDFTLKISRVEADDVGVYYCMQS

LQTPWTFGHGTKVEIKR
```

Location of the m906 VL Domain CDRs

| Convention: | IMGT | Kabat |
|---|---|---|
| CDR1 | 27-37 | 24-39 |
| CDR2 | 55-57 | 55-61 |
| CDR3 | 94-103 | 94-102 |

Provided herein are ADCs that include a drug conjugated to a CD56-specific monoclonal antibody, or an antigen-binding fragment thereof, wherein the monoclonal antibody or antigen-binding fragment thereof comprises a variable heavy (VH) domain and a variable light (VL) domain. In some embodiments, The VH domain of the antibody comprises at least a portion of the amino acid sequence set forth herein as SEQ ID NO: 2 or SEQ ID NO: 6, such as one or more (such as all three) CDR sequences from SEQ ID NO: 2 or SEQ ID NO: 6, such as one or more CDRs according to IMGT, Kabat or Chothia. In some embodiments, the VL domain of the antibody comprises at least a portion of the amino acid sequence set forth herein as SEQ ID NO: 4 or SEQ ID NO: 8, such as one or more (such as all three) CDR sequences from SEQ ID NO: 4 or SEQ ID NO: 8, such as one or more CDRs according to IMGT, Kabat or Chothia.

In particular embodiments, the VH domain comprises amino acid residues 26-33, 51-59 and 97-111; or amino acid residues 31-35, 50-66 and 99-110 of SEQ ID NO: 6 and the VL domain comprises amino acid residues 27-37, 55-57 and 94-103; or amino acid residues 24-39, 55-61 and 94-102 of SEQ ID NO: 8. In other particular embodiments, the VH domain comprises amino acid residues 26-35, 53-61 and 100-114; or amino acid residues 31-37, 52-69 and 102-113 of SEQ ID NO: 2 and the VL domain comprises amino acid residues 27-32, 50-52 and 89-97; or amino acid residues 24-34, 50-56 and 89-96 of SEQ ID NO: 4.

In some examples of the ADC, the VH domain comprises an amino acid sequence at least 80%, at least 85%, at least 90%, at least 95%, at least 96%, at least 97%, at least 98% or at least 99% identical to SEQ ID NO: 6 and/or the VL domain comprises an amino acid sequence at least 80%, at least 85%, at least 90%, at least 95%, at least 96%, at least 97%, at least 98% or at least 99% identical to SEQ ID NO: 8. In particular non-limiting examples, the VH domain comprises the amino acid sequence of SEQ ID NO: 6 and/or the VL domain comprises the amino acid sequence of SEQ ID NO: 8.

In other examples, the VH domain comprises an amino acid sequence at least 80%, at least 85%, at least 90%, at least 95%, at least 96%, at least 97%, at least 98% or at least 99% identical to SEQ ID NO: 2 and/or the VL domain comprises an amino acid sequence at least 80%, at least 85%, at least 90%, at least 95%, at least 96%, at least 97%, at least 98% or at least 99% identical to SEQ ID NO: 4. In particular non-limiting examples, the VH domain comprises the amino acid sequence of SEQ ID NO: 2 and/or the VL domain comprises the amino acid sequence of SEQ ID NO: 4.

In some embodiments of the ADC, the drug comprises a cytotoxic agent, such as an interstrand crosslinking agent, an anti-mitotic agent or an anti-microtubule agent. In some examples, the interstrand crosslinking agent comprises a pyrrolobenzodiazepine (PBD), such as a PBD dimer.

In some embodiments of the ADC, the antigen-binding fragment is an Fab fragment, an Fab' fragment, an F(ab)'$_2$ fragment, a single chain variable fragment (scFv) or a disulfide stabilized variable fragment (dsFv). In some embodiments, the monoclonal antibody is an IgG.

In some embodiments of the ADC, the monoclonal antibody, or antigen-binding fragment thereof, is a fully human antibody. In other embodiments, the monoclonal antibody, or antigen-binding fragment thereof, is chimeric or synthetic.

Also provided herein are compositions comprising an ADC as disclosed herein and a pharmaceutically acceptable carrier.

Further provided herein are compositions that include an ADC as disclosed herein and a monoclonal antibody, or antigen-binding fragment thereof, as disclosed herein (i.e. an antibody or fragment that is not conjugated to a drug). In some embodiments, the composition includes an ADC in which the antibody portion includes the CDR sequences of antibody m906. In some embodiments, the composition includes a monoclonal antibody, or antigen-binding fragment thereof, that includes the CDR sequences of m900. In particular embodiments, the composition includes an ADC in which the antibody portion includes the CDR sequences of antibody m906, and a monoclonal antibody, or antigen-binding fragment thereof, that includes the CDR sequences of m900.

Thus, in some embodiments, the composition includes (1) an ADC comprising a drug conjugated to a first CD56-specific monoclonal antibody or antigen-binding fragment thereof that comprises a VH domain comprising amino acid residues 26-33, 51-59 and 97-111; or amino acid residues 31-35, 50-66 and 99-110 of SEQ ID NO: 6 and a VL domain comprising amino acid residues 27-37, 55-57 and 94-103; or amino acid residues 24-39, 55-61 and 94-102 of SEQ ID NO: 8 (the CDR sequences of the m906 antibody); and (2) a second CD56-specific monoclonal antibody or antigen-binding fragment thereof, wherein the second CD56-specific monoclonal antibody or antigen-binding fragment comprises a VH domain comprising amino acid residues 26-35, 53-61 and 100-114; or amino acid residues 31-37, 52-69 and 102-113 of SEQ ID NO: 2 and a VL domain comprising amino acid residues 27-32, 50-52 and 89-97; or amino acid residues 24-34, 50-56 and 89-96 of SEQ ID NO: 4 (the CDRs sequences of antibody m900). In some embodiments, the compositions further include a pharmaceutically acceptable carrier.

In some embodiments of the disclosed compositions, the amino acid sequence of the VH domain of the second CD56-specific monoclonal antibody is at least 80%, at least 85%, at least 90%, at least 95%, at least 96%, at least 97%, at least 98% or at least 99% identical to SEQ ID NO: 2 and/or the amino acid sequence of the VL domain of the second CD56-specific monoclonal antibody is at least 80%, at least 85%, at least 90%, at least 95%, at least 96%, at least 97%, at least 98% or at least 99% identical to SEQ ID NO: 4. In some examples, the amino acid sequence of the VH domain of the second CD56-monoclonal antibody comprises SEQ ID NO: 2 and/or the amino acid sequence of the VL domain of the second CD56-monoclonal antibody comprises SEQ ID NO: 4.

In some embodiments of the disclosed compositions, the antigen-binding fragment is an Fab fragment, an Fab' fragment, an F(ab)'$_2$ fragment, a single chain variable fragment (scFv) or a disulfide stabilized variable fragment (dsFv). In some embodiments, the monoclonal antibody is an IgG. In some embodiments, the monoclonal antibody, or antigen-binding fragment thereof, is a fully human antibody. In other embodiments, the monoclonal antibody, or antigen-binding fragment thereof, is chimeric or synthetic.

Also provided herein are methods of treating a subject having a CD56-positive cancer. In some embodiments, the methods include selecting a subject with a CD56-positive cancer and administering to the subject a therapeutically effective amount of an ADC or composition disclosed herein.

Further provided are methods of inhibiting tumor growth or metastasis of a CD56-positive cancer in a subject. In some embodiments, the methods include selecting a subject with a CD56-positive cancer and administering to the subject an ADC or composition disclosed herein.

In some embodiments of the methods, the CD56-positive cancer is a neuroblastoma, multiple myeloma, acute myeloid leukemia, Wilms tumor, ovarian cancer or small cell lung cancer, or any other tumor expressing CD56.

V. Monoclonal Antibodies and Antigen-Binding Fragments Thereof

The monoclonal antibodies disclosed herein can be of any isotype. The monoclonal antibody can be, for example, an IgM or an IgG antibody, such as IgG$_1$ or an IgG$_2$. The class of an antibody that specifically binds CD56 can be switched with another (for example, IgG can be switched to IgM), according to well-known procedures. Class switching can also be used to convert one IgG subclass to another, such as from IgG$_1$ to IgG$_2$.

Antibody fragments are also encompassed by the present disclosure, such as single-domain antibodies (e.g., VH domain antibodies), Fab, F(ab')$_2$, and Fv. These antibody fragments retain the ability to selectively bind with the antigen. These antigen-binding fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, a genetically engineered fragment containing the variable region of the light chain and the variable region of the heavy chain expressed as two chains;

(5) Single chain antibody (such as scFv), a genetically engineered molecule containing the variable region of the light chain, the variable region of the heavy chain, linked by a suitable polypeptide linker as a genetically fused single chain molecule;

(6) A dimer of a single chain antibody (scFV$_2$), defined as a dimer of a scFv (also known as a "miniantibody"); and (7) VH single-domain antibody, an antibody fragment consisting of the heavy chain variable domain.

Methods of making these fragments are known in the art (see for example, Harlow and Lane, *Antibodies: A Laboratory Manual*, Cold Spring Harbor Laboratory, New York, 1988).

In some cases, antibody fragments can be prepared by proteolytic hydrolysis of the antibody or by expression in a host cell (such as *E. coli*) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. Nos. 4,036,945 and 4,331,647).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

One of skill will realize that conservative variants of the antibodies can be produced. Such conservative variants employed in antibody fragments, such as dsFv fragments or in scFv fragments, will retain critical amino acid residues necessary for correct folding and stabilizing between the V$_H$ and the V$_L$ regions, and will retain the charge characteristics of the residues in order to preserve the low pI and low toxicity of the molecules Amino acid substitutions (such as at most one, at most two, at most three, at most four, or at most five amino acid substitutions) can be made in the V$_H$ and/or the V$_L$ regions to increase yield. Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

VI. Antibody-Drug Conjugates (ADCs)

ADCs are compounds comprised of a tumor antigen-specific antibody and a drug, typically a cytotoxic agent, such as an anti-microtubule agent or cross-linking agent. Because ADCs are capable of specifically targeting cancer cells, the drug can be much more potent than agents used for standard chemotherapy. The most common cytotoxic drugs currently used with ADCs have an IC$_{50}$ that is 100- to 1000-fold more potent than conventional chemotherapeutic agents. Common cytotoxic drugs include anti-microtubule agents, such as maytansinoids and auristatins (such as auristatin E and auristatin F). Other cytotoxins for use with ADCs include pyrrolobenzodiazepines (PDBs), which covalently bind the minor groove of DNA to form interstrand crosslinks. In many instances, ADCs comprise a 1:2 to 1:4 ratio of antibody to drug (Bander, *Clinical Advances in Hematology & Oncology* 10(8; suppl 10):3-7, 2012).

The antibody and drug can be linked by a cleavable or non-cleavable linker. However, in some instances, it is desirable to have a linker that is stable in the circulation to prevent systemic release of the cytotoxic drug that could result in significant off-target toxicity. Non-cleavable linkers prevent release of the cytotoxic agent before the ADC is internalized by the target cell. Once in the lysosome, digestion of the antibody by lysosomal proteases results in the release of the cytotoxic agent (Bander, *Clinical Advances in Hematology & Oncology* 10(8; suppl 10):3-7, 2012).

One method for site-specific and stable conjugation of a drug to a monoclonal antibody is via glycan engineering. Monoclonal antibodies have one conserved N-linked oligosaccharide chain at the Asn297 residue in the CH2 domain of each heavy chain (Qasba et al., *Biotechnol Prog* 24:520-526, 2008). Using a mutant β1,4-galactosyltransferase enzyme (Y289L-Gal-T1; U.S. Patent Application Publication Nos. 2007/0258986 and 2006/0084162, herein incorporated by reference), 2-keto-galactose is transferred to free GlcNAc residues on the antibody heavy chain to provide a chemical handle for conjugation.

The oligosaccharide chain attached to monoclonal antibodies can be classified into three groups based on the terminal galactose residues—fully galactosylated (two galactose residues; IgG-G2), one galactose residue (IgG-G1) or completely degalactosylated (IgG-G0). Treatment of a monoclonal antibody with β1,4-galactosidase converts the antibody to the IgG-G0 glycoform. The mutant β1,4-galactosyltransferase enzyme is capable of transferring 2-keto-galactose or 2-azido-galactose from their respective UDP derivatives to the GlcNAc residues on the IgG-G1 and IgG-G0 glycoforms. The chemical handle on the transferred sugar enables conjugation of a variety of molecules to the monoclonal antibody via the glycan residues (Qasba et al., *Biotechnol Prog* 24:520-526, 2008).

Provided herein are ADCs that include a drug (such as a cytotoxic agent) conjugated to a monoclonal antibody that binds (such as specifically binds) CD56. In some embodiments, the drug is a small molecule. In some examples, the drug is a cross-linking agent, an anti-microtubule agent and/or anti-mitotic agent, or any cytotoxic agent suitable for mediating killing of tumor cells. Exemplary cytotoxic agents include, but are not limited to, a PDB, an auristatin, a maytansinoid, dolastatin, calicheamicin, nemorubicin and its derivatives, PNU-159682, anthracycline, duocarmycin, vinca alkaloid, taxane, trichothecene, CC1065, camptothecin, elinafide, a combretastain, a dolastatin, a duocarmycin, an enediyne, a geldanamycin, an indolino-benzodiazepine dimer, a puromycin, a tubulysin, a hemiasterlin, a spliceostatin, or a pladienolide, as well as stereoisomers, isosteres, analogs, and derivatives thereof that have cytotoxic activity.

In some embodiments, the ADC comprises a pyrrolobenzodiazepine (PBD). The natural product anthramycin (a PBD) was first reported in 1965 (Leimgruber et al., *J Am Chem Soc,* 87:5793-5795, 1965; Leimgruber et al., *J Am Chem Soc,* 87:5791-5793, 1965). Since then, a number of PBDs, both naturally-occurring and synthetic analogues, have been reported (Gerratana, *Med Res Rev* 32(2):254-293, 2012; and U.S. Pat. Nos. 6,884,799; 7,049,311; 7,067,511; 7,265,105; 7,511,032; 7,528,126; and 7,557,099). As one example, PDB dimers recognize and bind to specific DNA sequences, and have been shown to be useful as cytotoxic agents. PBD dimers have been conjugated to antibodies and the resulting ADC shown to have anti-cancer properties (see, for example, US 2010/0203007). Exemplary linkage sites on the PBD dimer include the five-membered pyrrolo ring, the tether between the PBD units, and the N10-C11 imine group (see WO 2009/016516; US 2009/304710; US 2010/047257; US 2009/036431; US 2011/0256157; and WO 2011/130598).

In some embodiments, the ADC comprises an antibody conjugated to one or more maytansinoid molecules. Maytansinoids are derivatives of maytansine, and are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinoids are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

In some embodiments, the ADC includes an antibody conjugated to a dolastatin or auristatin, or an analog or derivative thereof (see U.S. Pat. Nos. 5,635,483; 5,780,588; 5,767,237; and 6,124,431). Auristatins are derivatives of the marine mollusk compound dolastatin-10. Dolastatins and auristatins have been shown to interfere with microtubule dynamics, GTP hydrolysis, and nuclear and cellular division (Woyke et al., *Antimicrob Agents and Chemother* 45(12): 3580-3584, 2001) and have anticancer (U.S. Pat. No. 5,663, 149) and antifungal activity (Pettit et al., *Antimicrob Agents Chemother* 42:2961-2965, 1998). Exemplary dolastatins and auristatins include, but are not limited to, dolastatin 10, auristatin E, auristatin F, auristatin EB (AEB), auristatin EFP (AEFP), MMAD (Monomethyl Auristatin D or monomethyl dolastatin 10), MMAF (Monomethyl Auristatin F or N-methylvaline-valine-dolaisoleuine-dolaproine-phenylalanine), MMAE (Monomethyl Auristatin E or N-methylvaline-valine-dolaisoleuine-dolaproine-norephedrine), 5-benzoylvaleric acid-AE ester (AEVB), and other auristatins (see, for example, U.S. Publication No. 2013/0129753).

In some embodiments, the ADC comprises an antibody conjugated to one or more calicheamicin molecules. The calicheamicin family of antibiotics, and analogues thereof, are capable of producing double-stranded DNA breaks at sub-picomolar concentrations (Hinman et al., *Cancer Res* 53:3336-3342, 1993; Lode et al., *Cancer Res* 58:2925-2928, 1998). Exemplary methods for preparing ADCs with a calicheamicin drug moiety are described in U.S. Pat. Nos. 5,712,374; 5,714,586; 5,739,116; and 5,767,285.

In some embodiments, the ADC comprises an anthracycline. Anthracyclines are antibiotic compounds that exhibit cytotoxic activity. It is believed that anthracyclines can operate to kill cells by a number of different mechanisms, including intercalation of the drug molecules into the DNA of the cell thereby inhibiting DNA-dependent nucleic acid synthesis; inducing production of free radicals which then react with cellular macromolecules to cause damage to the cells; and/or interactions of the drug molecules with the cell membrane. Non-limiting exemplary anthracyclines include doxorubicin, epirubicin, idarubicin, daunomycin, daunorubicin, doxorubicin, epirubicin, nemorubicin, valrubicin and mitoxantrone, and derivatives thereof. For example, PNU-159682 is a potent metabolite (or derivative) of nemorubicin (Quintieri et al., *Clin Cancer Res* 11(4):1608-1617, 2005). Nemorubicin is a semisynthetic analog of doxorubicin with a 2-methoxymorpholino group on the glycoside amino of doxorubicin (Grandi et al., *Cancer Treat Rev* 17:133, 1990; Ripamonti et al., *Br J Cancer* 65:703-707, 1992).

In some embodiments, the ADC can further include a linker. In some examples, the linker is a bifunctional or multifunctional moiety that can be used to link one or more drug moieties to an antibody to form an ADC. In some embodiments, ADCs are prepared using a linker having reactive functionalities for covalently attaching to the drug and to the antibody. For example, a cysteine thiol of an antibody can form a bond with a reactive functional group of a linker or a drug-linker intermediate to make an ADC.

In some examples, a linker has a functionality that is capable of reacting with a free cysteine present on an antibody to form a covalent bond. Exemplary linkers with such reactive functionalities include maleimide, haloacetamides, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates.

In some examples, a linker has a functionality that is capable of reacting with an electrophilic group present on an antibody. Examples of such electrophilic groups include, but are not limited to, aldehyde and ketone carbonyl groups. In some cases, a heteroatom of the reactive functionality of the linker can react with an electrophilic group on an antibody and form a covalent bond to an antibody unit. Non-limiting examples include hydrazide, oxime, amino, hydrazine, thiosemicarbazone, hydrazine carboxylate and arylhydrazide.

In some examples, the linker is a cleavable linker, which facilitates release of the drug. Examples of cleavable linkers include acid-labile linkers (for example, comprising hydrazone), protease-sensitive linkers (for example, peptidase-sensitive), photolabile linkers, and disulfide-containing linkers (Chari et al., *Cancer Res* 52:127-131, 1992; U.S. Pat. No. 5,208,020).

The ADCs disclosed herein can be used for the treatment of a CD56-positive cancer alone or in combination with another therapeutic agent and/or in combination with any standard therapy for the treatment of cancer (such as surgical resection of the tumor, chemotherapy or radiation therapy).

VII. Chimeric Antigen Receptors (CARs)

The disclosed monoclonal antibodies can also be used to produce CARs (also known as chimeric T cell receptors, artificial T cell receptors or chimeric immunoreceptors) and/or cytotoxic T lymphocytes (CTLs) engineered to express CARs. Generally, CARs include a binding moiety, an extracellular hinge and spacer element, a transmembrane region and an endodomain that performs signaling functions (Cartellieri et al., *J Biomed Biotechnol* 2010:956304, 2010). In many instances, the binding moiety is an antigen binding fragment of a monoclonal antibody, such as a scFv. Several different endodomains have been used to generate CARs. For example, the endodomain can consist of a signaling chain having an ITAM, such as CD3ζ or FcεRIγ. In some instances, the endodomain further includes the intracellular portion of at least one additional co-stimulatory domain, such as CD28 and/or CD137.

CTLs expressing CARs can be used to target a specific cell type, such as a tumor cell. Thus, the monoclonal antibodies disclosed herein can be used to engineer CTLs that express a CAR containing an antigen-binding fragment of a CD56-specific antibody, thereby targeting the engineered CTLs to CD56-expressing tumor cells. Engineered T cells have previously been used for adoptive therapy for some types of cancer (see, for example, Park et al., *Mol Ther* 15(4):825-833, 2007). The use of T cells expressing CARs is more universal than standard CTL-based immunotherapy because CTLs expressing CARs are HLA unrestricted and can therefore be used for any patient having a tumor that expresses the target antigen.

Accordingly, provided herein are CARs that include a CD56-specific monoclonal antibody, or antigen-binding fragment thereof, such as a scFv. Also provided are isolated nucleic acid molecules and vectors encoding the CARs, and host cells, such as CTLs, expressing the CARs. CTLs expressing CARs comprised of a CD56-specific monoclonal antibody (or antibody binding fragment) can be used for the treatment of cancers that express CD56, such as neuroblastoma, multiple myeloma, ovarian cancer, acute myeloid leukemia, Wilms tumor and small cell lung cancer.

VIII. Bispecific Antibodies

Bispecific antibodies are recombinant proteins comprised of antigen-binding fragments of two different monoclonal antibodies. Thus, bispecific antibodies bind two different antigens. Bispecific antibodies can be used for cancer immunotherapy by simultaneously targeting both CTLs (such as a CTL receptor component, for example CD3) and a tumor antigen. The CD56-specific monoclonal antibodies disclosed herein can be used to generate bispecific antibodies that target both CD56 and CTLs, thereby providing a means to treat CD56-expressing cancers.

Provided herein are bispecific monoclonal antibodies comprising a CD56-specific monoclonal antibody, or antigen-binding fragment thereof. In some embodiments, the bispecific monoclonal antibody further comprises a monoclonal antibody, or antigen-binding fragment thereof, that specifically binds a component of the T cell receptor, such as CD3. Also provided are isolated nucleic acid molecules and vectors encoding the bispecific antibodies, and host cells comprising the nucleic acid molecules or vectors. Bispecific antibodies comprising a CD56-specific antibody, or antigen-binding fragment thereof, can be used for the treatment of cancers that express CD56, such as neuroblastoma, multiple myeloma, ovarian cancer, acute myeloid leukemia, Wilms tumor and small cell lung cancer. Thus, provided herein are methods of treating a subject with cancer by selecting a subject with a cancer that expresses CD56, and administering to the subject a therapeutically effective amount of the CD56-targeting bispecific antibody.

IX. Immunoconjugates

The disclosed monoclonal antibodies specific for CD56 can be conjugated to a therapeutic agent or effector molecule. Immunoconjugates include, but are not limited to, molecules in which there is a covalent linkage of a therapeutic agent to an antibody. A therapeutic agent is an agent with a particular biological activity directed against a particular target molecule or a cell bearing a target molecule. One of skill in the art will appreciate that therapeutic agents can include various drugs such as vinblastine, daunomycin and the like, cytotoxins such as native or modified *Pseudomonas* exotoxin or diphtheria toxin, encapsulating agents (such as liposomes) that contain pharmacological compositions, radioactive agents such as $^{125}$I, $^{32}$P, $^{14}$C, $^{3}$H and $^{35}$S and other labels, target moieties and ligands.

The choice of a particular therapeutic agent depends on the particular target molecule or cell, and the desired biological effect. Thus, for example, the therapeutic agent can be a cytotoxin that is used to bring about the death of a particular target cell (such as a tumor cell). Conversely, where it is desired to invoke a non-lethal biological response, the therapeutic agent can be conjugated to a non-lethal pharmacological agent or a liposome containing a non-lethal pharmacological agent.

With the therapeutic agents and antibodies described herein, one of skill can readily construct a variety of clones containing functionally equivalent nucleic acids, such as nucleic acids which differ in sequence but which encode the same effector moiety or antibody sequence. Thus, the present disclosure provides nucleic acids encoding antibodies and conjugates and fusion proteins thereof.

Effector molecules can be linked to an antibody of interest using any number of means known to those of skill in the art. Both covalent and noncovalent attachment means may be used. The procedure for attaching an effector molecule to an antibody varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule. Alternatively, the antibody is derivatized to expose or attach additional reactive functional groups. The derivatization may involve attachment of any of a number of known linker molecules. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (such as through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site.

In view of the large number of methods that have been reported for attaching a variety of radiodiagnostic compounds, radiotherapeutic compounds, labels (such as enzymes or fluorescent molecules), drugs, toxins, and other agents to antibodies one skilled in the art will be able to determine a suitable method for attaching a given agent to an antibody or other polypeptide.

The antibodies or antibody fragments disclosed herein can be derivatized or linked to another molecule (such as another peptide or protein). In general, the antibodies or portion thereof is derivatized such that the binding to the target antigen is not affected adversely by the derivatization or labeling. For example, the antibody can be functionally linked (by chemical coupling, genetic fusion, noncovalent association or otherwise) to one or more other molecular entities, such as another antibody (for example, a bispecific antibody or a diabody), a detection agent, a pharmaceutical agent, and/or a protein or peptide that can mediate association of the antibody or antibody portion with another molecule (such as a streptavidin core region or a polyhistidine tag).

One type of derivatized antibody is produced by crosslinking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are commercially available.

The antibody can be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, green fluorescent protein (GFP) and yellow fluorescent protein (YFP). An antibody or antigen binding fragment can also be conjugated with enzymes that are useful for detection, such as horseradish peroxidase, β-galactosidase, luciferase, alkaline phosphatase, glucose oxidase and the like. When an antibody or antigen binding fragment is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody or antigen binding fragment may also be conjugated with biotin, and detected through indirect measurement of avidin or streptavidin binding. It should be noted that the avidin itself can be conjugated with an enzyme or a fluorescent label.

An antibody may be labeled with a magnetic agent, such as gadolinium. Antibodies can also be labeled with lanthanides (such as europium and dysprosium), and manganese. Paramagnetic particles such as superparamagnetic iron oxide are also of use as labels. An antibody may also be labeled with a predetermined polypeptide epitopes recognized by a secondary reporter (such as leucine zipper pair sequences, binding sites for secondary antibodies, metal binding domains, epitope tags). In some embodiments, labels are attached by spacer arms of various lengths to reduce potential steric hindrance.

An antibody can also be labeled with a radiolabeled amino acid. The radiolabel may be used for both diagnostic and therapeutic purposes. For instance, the radiolabel may be used to detect CD56 by x-ray, emission spectra, or other diagnostic techniques. Examples of labels for polypeptides include, but are not limited to, the following radioisotopes or radionucleotides: $^{3}$H, $^{14}$C, $^{15}$N, $^{35}$S, $^{90}$Y, $^{99}$Tc, $^{111}$In, $^{125}$I, $^{131}$I.

An antibody can also be derivatized with a chemical group such as polyethylene glycol (PEG), a methyl or ethyl group, or a carbohydrate group. These groups may be useful to improve the biological characteristics of the antibody, such as to increase serum half-life or to increase tissue binding.

Toxins can be employed with the monoclonal antibodies described herein to produce immunotoxins. Exemplary toxins include ricin, abrin, diphtheria toxin and subunits thereof, as well as botulinum toxins A through F. These toxins are readily available from commercial sources (for example, Sigma Chemical Company, St. Louis, Mo.). Contemplated toxins also include variants of the toxins described herein (see, for example, see, U.S. Pat. Nos. 5,079,163 and 4,689,401). In one embodiment, the toxin is *Pseudomonas* exotoxin (PE) (U.S. Pat. No. 5,602,095). As used herein "*Pseudomonas* exotoxin" refers to a full-length native (naturally occurring) PE or a PE that has been modified. Such modifications can include, but are not limited to, elimination of domain Ia, various amino acid deletions in domains Ib, II and III, single amino acid substitutions and the addition of one or more sequences at the carboxyl terminus (for example, see Siegall et al., *J. Biol. Chem.* 264:14256-14261, 1989).

PE employed with the monoclonal antibodies described herein can include the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell. Cytotoxic fragments of PE include PE40, PE38, and PE35. For additional description of PE and variants thereof, see for example, U.S. Pat. Nos. 4,892,827; 5,512, 658; 5,602,095; 5,608,039; 5,821,238; and 5,854,044; PCT Publication Nos. WO 99/51643 and WO 2014/052064; Pai et al., *Proc. Natl. Acad. Sci. USA* 88:3358-3362, 1991; Kondo et al., *J. Biol. Chem.* 263:9470-9475, 1988; Pastan et al., *Biochim. Biophys. Acta* 1333:C1-C6, 1997.

Also contemplated herein are protease-resistant PE variants and PE variants with reduced immunogenicity, such as, but not limited to PE-LR, PE-6X, PE-8X, PE-LR/6X and PE-LR/8X (see, for example, Weldon et al., *Blood* 113(16): 3792-3800, 2009; Onda et al., *Proc Natl Acad Sci USA* 105(32):11311-11316, 2008; and PCT Publication Nos. WO 2007/016150, WO 2009/032954 and WO 2011/032022, which are herein incorporated by reference).

In some examples, the PE is a variant that is resistant to lysosomal degradation, such as PE-LR (Weldon et al., *Blood* 113(16):3792-3800, 2009; PCT Publication No. WO 2009/ 032954). In other examples, the PE is a variant designated PE-LR/6X (PCT Publication No. WO 2011/032022). In other examples, the PE variant is PE with reducing immunogenicity. In yet other examples, the PE is a variant designated PE-LR/8M (PCT Publication No. WO 2011/ 032022).

Modification of PE may occur in any previously described variant, including cytotoxic fragments of PE (for example, PE38, PE-LR and PE-LR/8M). Modified PEs may include any substitution(s), for one or more amino acid residues within one or more T-cell epitopes and/or B cell epitopes of PE.

The antibodies described herein can also be used to target any number of different diagnostic or therapeutic compounds to cells expressing CD56 on their surface. Thus, an antibody of the present disclosure can be attached directly or via a linker to a drug that is to be delivered directly to cells expressing cell-surface CD56. This can be done for therapeutic, diagnostic or research purposes. Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides.

Alternatively, the molecule linked to an anti-CD56 antibody can be an encapsulation system, such as a liposome or micelle that contains a therapeutic composition such as a drug, a nucleic acid (for example, an antisense nucleic acid), or another therapeutic moiety that is preferably shielded from direct exposure to the circulatory system. Means of preparing liposomes attached to antibodies are well known to those of skill in the art (see, for example, U.S. Pat. No. 4,957,735; Connor et al., *Pharm. Ther.* 28:341-365, 1985).

Antibodies described herein can also be covalently or non-covalently linked to a detectable label. Detectable labels suitable for such use include any composition detectable by spectroscopic, photochemical, biochemical, immunochemical, electrical, optical or chemical means. Useful labels include magnetic beads, fluorescent dyes (for example, fluorescein isothiocyanate, Texas red, rhodamine, green fluorescent protein, and the like), radiolabels (for example, $^3$H, $^{125}$I, $^{35}$S, $^{14}$C, or $^{32}$P), enzymes (such as horseradish peroxidase, alkaline phosphatase and others commonly used in an ELISA), and colorimetric labels such as colloidal gold or colored glass or plastic (such as polystyrene, polypropylene, latex, and the like) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

X. Compositions and Methods of Use

Compositions are provided that include one or more of the disclosed antibodies that bind (for example specifically bind) CD56 in a carrier. Compositions comprising ADCs, CARs (and CTLs comprising CARs), bispecific antibodies and immunoconjugates are also provided. The compositions can be prepared in unit dosage forms for administration to a subject. The amount and timing of administration are at the discretion of the treating clinician to achieve the desired outcome. The antibody, ADC, CAR, CTL, bispecific antibody or immunoconjugate can be formulated for systemic or local (such as intra-tumor) administration. In one example, the antibody is formulated for parenteral administration, such as intravenous administration.

The compositions for administration can include a solution of the antibody, ADC, CAR, CTL, bispecific antibody or immunoconjugate in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical pharmaceutical composition for intravenous administration includes about 0.1 to 10 mg of antibody (or ADC, CAR, bispecific antibody or immunoconjugate) per subject per day. Dosages from 0.1 up to about 100 mg per subject per day may be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remington's Pharmaceutical Science*, 19th ed., Mack Publishing Company, Easton, Pa. (1995).

Antibodies (or other therapeutic molecules) may be provided in lyophilized form and rehydrated with sterile water before administration, although they are also provided in sterile solutions of known concentration. The antibody solution is then added to an infusion bag containing 0.9% sodium chloride, USP, and in some cases administered at a dosage of from 0.5 to 15 mg/kg of body weight, such as about 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg or 15 mg/kg. Considerable experience is available in the art in the administration of antibody drugs, which have been marketed in the U.S. since the approval of RITUXAN™ in 1997. Antibodies, ADCs, CARs, bispecific antibodies or immunoconjugates can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the antibody-based compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

A. Therapeutic Methods

The antibodies, compositions, CARs (and CTLs expressing CARs), ADCs, bispecific antibodies and immunoconjugates disclosed herein can be administered to slow or inhibit the growth of tumor cells or inhibit the metastasis of tumor cells, such as neuroblastoma, multiple myeloma, ovarian or small cell lung tumors. In these applications, a therapeutically effective amount of a composition is administered to a subject in an amount sufficient to inhibit growth, replication or metastasis of cancer cells, or to inhibit a sign or a symptom of the cancer. Suitable subjects may include those diagnosed with a cancer that expresses CD56, such as, but not limited to, neuroblastoma, multiple myeloma, ovarian cancer, acute myeloid leukemia, Wilms tumor or small cell lung cancer.

Provided herein is a method of treating a subject having a CD56-positive cancer by selecting a subject with a CD56-positive cancer and administering to the subject a therapeutically effective amount of an antibody, ADC, CAR (e.g. a CTL expressing a CAR), bispecific antibody, immunoconjugate or composition disclosed herein. Also provided herein is a method of inhibiting tumor growth or metastasis of a CD56-positive cancer in a subject by selecting a subject with a CD56-positive cancer and administering to the subject a therapeutically effective amount of an antibody, ADC, CAR (e.g. a CTL expressing a CAR), bispecific antibody, immunoconjugate or composition disclosed herein. In some embodiments, the CD56-positive cancer is neuroblastoma, multiple myeloma, ovarian cancer, acute myeloid leukemia, Wilms tumor or small cell lung cancer.

A therapeutically effective amount of a CD56-specific antibody, ADC, CAR (e.g. a CTL expressing a CAR), bispecific antibody, immunoconjugate or composition will depend upon the severity of the disease and the general state of the patient's health. A therapeutically effective amount of the antibody-based composition is that which provides either subjective relief of a symptom(s) or an objectively identifiable improvement as noted by the clinician or other qualified observer.

Administration of the antibodies, ADCs, CARs, immunoconjugates, bispecific antibodies and compositions disclosed herein can also be accompanied by administration of other anti-cancer agents or therapeutic treatments (such as surgical resection of a tumor). Any suitable anti-cancer agent can be administered in combination with the antibodies, compositions and immunoconjugates disclosed herein. Exemplary anti-cancer agents include, but are not limited to, chemotherapeutic agents, such as, for example, mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones (e.g. anti-androgens) and anti-angiogenesis agents. Other anti-cancer treatments include radiation therapy and other antibodies that specifically target cancer cells.

Non-limiting examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine).

Non-limiting examples of antimetabolites include folic acid analogs (such as methotrexate), pyrimidine analogs (such as 5-FU or cytarabine), and purine analogs, such as mercaptopurine or thioguanine.

Non-limiting examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitomycin C), and enzymes (such as L-asparaginase).

Non-limiting examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide).

Non-limiting examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone). Examples of the most commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol.

Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

Another common treatment for some types of cancer is surgical treatment, for example surgical resection of the cancer or a portion of it. Another example of a treatment is radiotherapy, for example administration of radioactive material or energy (such as external beam therapy) to the tumor site to help eradicate the tumor or shrink it prior to surgical resection.

B. Methods for Diagnosis and Detection

Methods are provided herein for detecting expression of CD56 in vitro or in vivo. In some cases, CD56 expression is detected in a biological sample. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. A biological sample is typically obtained from a mammal, such as a human or non-human primate.

In one embodiment, provided is a method of determining if a subject has a CD56-positive cancer by contacting a sample from the subject with a monoclonal antibody disclosed herein; and detecting binding of the antibody to the sample. An increase in binding of the antibody to the sample as compared to binding of the antibody to a control sample identifies the subject as having a CD56-positive cancer.

In another embodiment, provided is a method of confirming a diagnosis of a CD56-positive cancer in a subject by contacting a sample from a subject diagnosed with a CD56-positive cancer with a monoclonal antibody disclosed herein; and detecting binding of the antibody to the sample. An increase in binding of the antibody to the sample as compared to binding of the antibody to a control sample confirms the diagnosis of a CD56-positive cancer in the subject.

In some examples of the disclosed methods, the monoclonal antibody is directly labeled.

In some examples, the methods further include contacting a second antibody that specifically binds the monoclonal antibody with the sample; and detecting the binding of the second antibody. An increase in binding of the second antibody to the sample as compared to binding of the second antibody to a control sample detects a CD56-positive cancer in the subject or confirms the diagnosis of a CD56-positive cancer in the subject.

In some cases, the cancer is neuroblastoma, multiple myeloma, ovarian cancer, acute myeloid leukemia, Wilms tumor or small cell lung cancer, or any other type of cancer that expresses CD56.

In some examples, the control sample is a sample from a subject without cancer. In particular examples, the sample is a blood or tissue sample.

In some cases, the antibody that binds (for example specifically binds) CD56 is directly labeled with a detectable label. In another embodiment, the antibody that binds (for example, specifically binds) CD56 (the first antibody) is unlabeled and a second antibody or other molecule that can bind the antibody that specifically binds CD56 is labeled. As is well known to one of skill in the art, a second antibody is chosen that is able to specifically bind the specific species and class of the first antibody. For example, if the first antibody is a human IgG, then the secondary antibody may be an anti-human-IgG. Other molecules that can bind to antibodies include, without limitation, Protein A and Protein G, both of which are available commercially.

Suitable labels for the antibody or secondary antibody are described above, and include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}$I, $^{131}$I, $^{35}$S or $^{3}$H.

In an alternative embodiment, CD56 can be assayed in a biological sample by a competition immunoassay utilizing CD56 standards labeled with a detectable substance and an unlabeled antibody that specifically binds CD56. In this assay, the biological sample, the labeled CD56 standards and the antibody that specifically bind CD56 are combined and the amount of labeled CD56 standard bound to the unlabeled antibody is determined. The amount of CD56 in the biological sample is inversely proportional to the amount of labeled CD56 standard bound to the antibody that specifically binds CD56.

The immunoassays and method disclosed herein can be used for a number of purposes. In one embodiment, the antibody that specifically binds CD56 may be used to detect the production of CD56 in cells in cell culture. In another embodiment, the antibody can be used to detect the amount of CD56 in a biological sample, such as a tissue sample, or a blood or serum sample. In some examples, the CD56 is cell-surface CD56. In other examples, the CD56 is soluble CD56 (e.g. CD56 in a cell culture supernatant or soluble CD56 in a body fluid sample, such as a blood or serum sample).

In one embodiment, a kit is provided for detecting CD56 in a biological sample, such as a blood sample or tissue sample. For example, to confirm a cancer diagnosis in a subject, a biopsy can be performed to obtain a tissue sample for histological examination. Alternatively, a blood sample can be obtained to detect the presence of soluble CD56 protein or fragment. Kits for detecting a polypeptide will typically comprise a monoclonal antibody that specifically binds CD56, such as any of the antibodies disclosed herein. In some embodiments, an antibody fragment, such as a scFv fragment, a VH domain, or a Fab is included in the kit. In a further embodiment, the antibody is labeled (for example, with a fluorescent, radioactive, or an enzymatic label).

In one embodiment, a kit includes instructional materials disclosing means of use of an antibody that binds CD56. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting CD56 in a biological sample generally includes the steps of contacting the biological sample with an antibody which specifically reacts, under immunologically reactive conditions, to a CD56 polypeptide. The antibody is allowed to specifically bind under immunologically reactive conditions to form an immune complex, and the presence of the immune complex (bound antibody) is detected directly or indirectly.

Methods of determining the presence or absence of a cell surface marker are well known in the art. For example, the antibodies can be conjugated to other compounds including, but not limited to, enzymes, magnetic beads, colloidal magnetic beads, haptens, fluorochromes, metal compounds, radioactive compounds or drugs. The antibodies can also be utilized in immunoassays such as but not limited to radioimmunoassays (RIAs), ELISA, or immunohistochemical assays. The antibodies can also be used for fluorescence activated cell sorting (FACS). FACS employs a plurality of color channels, low angle and obtuse light-scattering detection channels, and impedance channels, among other more sophisticated levels of detection, to separate or sort cells (see U.S. Pat. No. 5,061,620). Any of the monoclonal antibodies that bind CD56, as disclosed herein, can be used in these assays. Thus, the antibodies can be used in a conventional immunoassay, including, without limitation, an ELISA, an RIA, FACS, tissue immunohistochemistry, Western blot or immunoprecipitation.

The following examples are provided to illustrate certain particular features and/or embodiments. These examples should not be construed to limit the disclosure to the particular features or embodiments described.

EXAMPLES

Example 1: Materials and Methods

This example describes the experimental procedures used for the studies described in Example 2.

Identification of CD56 Antibodies from a Phage Library

CD56 full-length cDNA (isoform 2) in the pCMV vector was purchased from OriGene (Rockville, Md.), and was used as the source for constructing expression vectors of CD56 fragments. DNAs encoding the following CD56 fragments were amplified flanked with BamHI and HindIII sites: CD56-G1-5 (residues 20-495), 475 amino acids; CD56-FN1,2 (residues 496-720), 224 amino acids; and whole ectodomain (residues 20-720), 700 amino acids. The amplified DNAs were ligated with the psectag2A vector that was digested with BamHI and HindIII. After the sequences of the expression vectors were confirmed, the recombinant proteins were expressed transiently in 293 FREESTYLE™ cultures. Recombinant CD56 fragments were purified from the conditioned culture media with a Ni-NTA column. Proteins were dialyzed into PBS. The whole ectodomain of CD56 was used for panning of the naïve human Fab phage library ($5 \times 10^{10}$ unique clones). Briefly, the CD56 ectodomain was coated on a Maxisorp plate and phage was added to the CD56 pre-absorbed surface. After washes with PBST, the eluted phages were used to rescue exponentially growing TG1 cells. The final two clones, m900 and m906, with good affinity to CD56 were further characterized. Both antibodies were converted into scFv and human IgG1 formats.

Expression and Purification of Antibodies

Expression of Fab and scFv were performed in HB2151 bacterial culture according to known procedures (Feng et al., *Mol Cancer Ther* 5(1):114-120, 2006). Conversion and preparation of IgG1s were done according to a standard protocol described in Feng et al. (*Mol Cancer Ther* 5(1): 114-120, 2006). To prepare defucosylated IgG1, a fucosylation inhibitor, kifunnsine, was used. The defucosylated IgG was purified on a protein G column. All antibody fragments and IgG1s were dialyzed into PBS.

Measurement of Binding with ELISA

Protein was coated on ELISA plate wells at 50 ng/well in PBS at 4° C. overnight. After blocking of unbound surface with 2% non-fat dried milk in PBST, serially diluted antibody solutions were added, and incubated for 2 hours at 37° C. The bound human antibodies were detected with goat anti-human Fc specific IgG conjugated with horseradish peroxidase. The enzyme activity was measured with the subsequent addition of substrate ABTS and signal read was at OD 405 nm.

Measurement of Antibody Affinity with Surface Plasmon Resonance

The binding affinity of the Fabs to CD56 ectodomain was measured on a BIACORE™ X100 instrument (GE Healthcare). Purified human CD56 ectodomain was diluted in 10 mM sodium acetate buffer (pH 5.0) and immobilized on a CM5 biosensor chip using an amine coupling kit. The running buffer was HBS-EP (10 mM HEPES, pH 7.4, 150 mM NaCl, 3 mM EDTA, 0.05% surfactant P20). Fabs diluted with the running buffer were allowed to flow through the cells at concentrations ranging from 0.05 nM to 500 nM. After 10 minutes of dissociation, the chip was regenerated with 10 mM glycine, pH 3.0, 0.5M NaCl. The data were fitted with 1:1 binding model and the dissociation rate constant was estimated with BIAevaluation software.

Cell Culture, Growth and Internalization Test

Neuroblastoma cell lines, IMR5 and SK-N-AS, were maintained in RPMI1640 supplemented with 20% fetal bovine serum (FBS) and penicillin/streptomycin. For the growth test with ADCs, 7000 cells/well were seeded in 96-well clear bottom plates. Cells were allowed to attach to the plate overnight, and on the next day they were treated with the ADCs at designated final concentrations. Each concentration was repeated in triplicate. After 4 days of growth, the viability of cells were monitored by adding reagent from CELLTITER 96™ AQueous One Solution Cell Proliferation Assay (Promega), and incubated for 1 hour at 37° C. The viability of cells was recorded at OD 490 nm.

For the measurement of CD56 down-regulation with flow cytometry, cells were seeded in a 6-well plate at a density of 0.6 million cells/well. After overnight culture, the CD56 IgG1, m900 or m906, were added to cells at 50 nM. Cells in control wells were treated with 50 nM of isotype control human antibody. After overnight incubation, cells were detached with Cell Dissociation Buffer (Invitrogen) and washed in PBS. The CD56 surface level was measured by incubation of cells with a commercially available CD56 mouse antibody (Clone 555514, BD Bioscience), on ice for 1 hour. An anti-caspase 9 mouse antibody was used as a negative control for the staining. The mouse antibody was detected with a goat anti-mouse Fc polyclonal antibody coupled with FITC. Cells were processed in FACSCalibur.

For the internalization test with the combination of primary antibody (m900 and m906) and hFab-ZAP (Advanced Targeting Systems), the cells were set up in 96-well plates, similar to the procedure for the growth test. Cells were treated with 5 nM of hFab-ZAP with a range (5 to 0.2 nM) of the primary antibody. An isotype-controlled antibody was included at 5 nM with 5 nM hFab-ZAP as a negative control. The growth of cells was monitored as above.

Preparation of Antibody-drug Conjugates m900 or m906 IgG1 was conjugated with PBD-MC (pyrrolobenzodiazepine dimmer with maleimide) with a simplified protocol from Lyon et al. (*Methods Enzymol* 502:123-138, 2012), which involves conjugation to cysteine residues of IgG with thio-reactive drug-linkers. PBD-MC was purchased from TCRS (The Chemistry Resource Solution, LLC, PA). Briefly, the IgGs were bound to protein G resin, and reduced in 10 mM TCEP/PBS/1 mM EDTA for 1 hour at room temperature. The excess TCEP was washed off, and the IgG-bound protein G resin was resuspended in 45% propylene glycol (PPG) in PBS/EDTA. The drug PBD-MC was reconstituted in DMSO/PPG (1:1 in v:v). For each 10 mg of IgG in 5 ml PPG/PBS, 300 μg PBD-MC in approximately 300 μl DMSO/PPG was added. This buffer condition kept both IgG and the drug soluble. The conjugation reaction was carried out at room temperature for two hours. The resin slurry was washed with PPG/PBS buffer with gradually decreasing PPG concentrations, and finally in PBS. The conjugated ADCs were eluted with acidic buffer and dialyzed into PBS. The final ADCs were resolved in a SUPERDEX™ 200 10/300 GL size exclusion column.

ADCC Assays

Two types of ADCC assays were used. In the first assay, Jurkat cells engineered for stable expression of human CD16a (FcgRIIIa) (Promega) were used as the effector cells. These cells also have transcription factor NFAT (nuclear factor of activated T cells) and luciferase genes inserted. Upon the engaging of antibodies with CD16, NFAT DNA binding response is activated and drives the expression of luciferase activity, which can be measured with the addition of substrate Bio-Glo. This assay however, does not measure the actual lysis of the target cells. The effector to target cell ratio was 6:1 (E:75,000 to T:12,500 per well). The luciferase activity was read after 6 hours of co-incubation of cells with the test antibodies.

The second ADCC assay employed the standard protocol with purified peripheral blood mononuclear cells (PBMCs) from healthy humans as the effector cells (Feng et al., *Mol Cancer Ther* 8(5):1113-1118, 2009). Briefly, PMBCs were isolated from healthy donors with FICOLL-PAQUE™ Plus (GE Healthcare). Collections of blood from donors were approved by NCI-Frederick Research Donor Program. The viability of isolated cells was >95%. PBMC were seeded in a 96-well plate in RPMI+10% FBS at 500,000 cells/well. Cells were incubated at 37° C. and allowed to attach to the plate for three hours. Target cells, IMR5 or SK-N-AS cells, were trypsinized and resuspended into single cell suspensions. The target cells were incubated with various concentrations of antibody at room temperature for 30 minutes then added to effector cells at 10,000 cells/well. The ratio of effector and target cells was 50:1. The plate was centrifuged at 300 g for five minutes and incubated at 37° C. for 16 hours. The next day, an equal volume of CYTOTOX-ONE™ reagent (Promega) was added to each well. The lactate dehydrogenase (LDH) released from lysed cells converted CYTOTOX™ substrate to fluorescent resazurin, which was measured in a fluorometer (Ex 560 nm/Em 590 nm). The percentage of specific lysis was calculated as follows: (experimental treatment-effector cell control)/(high control-target cell control)×100%. Measurement of target cells alone treated with 1% Triton X-100 was used as high control. Each treatment was carried out in triplicated wells. Each assay plate included control wells.

Example 2: Characterization of CD56-Specific Antibody-Drug Conjugates

This example describes the identification and characterization of two fully human CD56 antibodies from a Fab phage library. The two antibodies, m900 and m906, bind to the fibronectin type III domain and IgG-like domains of CD56, respectively.

Identification and Characterization of CD56 Antibodies

Figure 12:
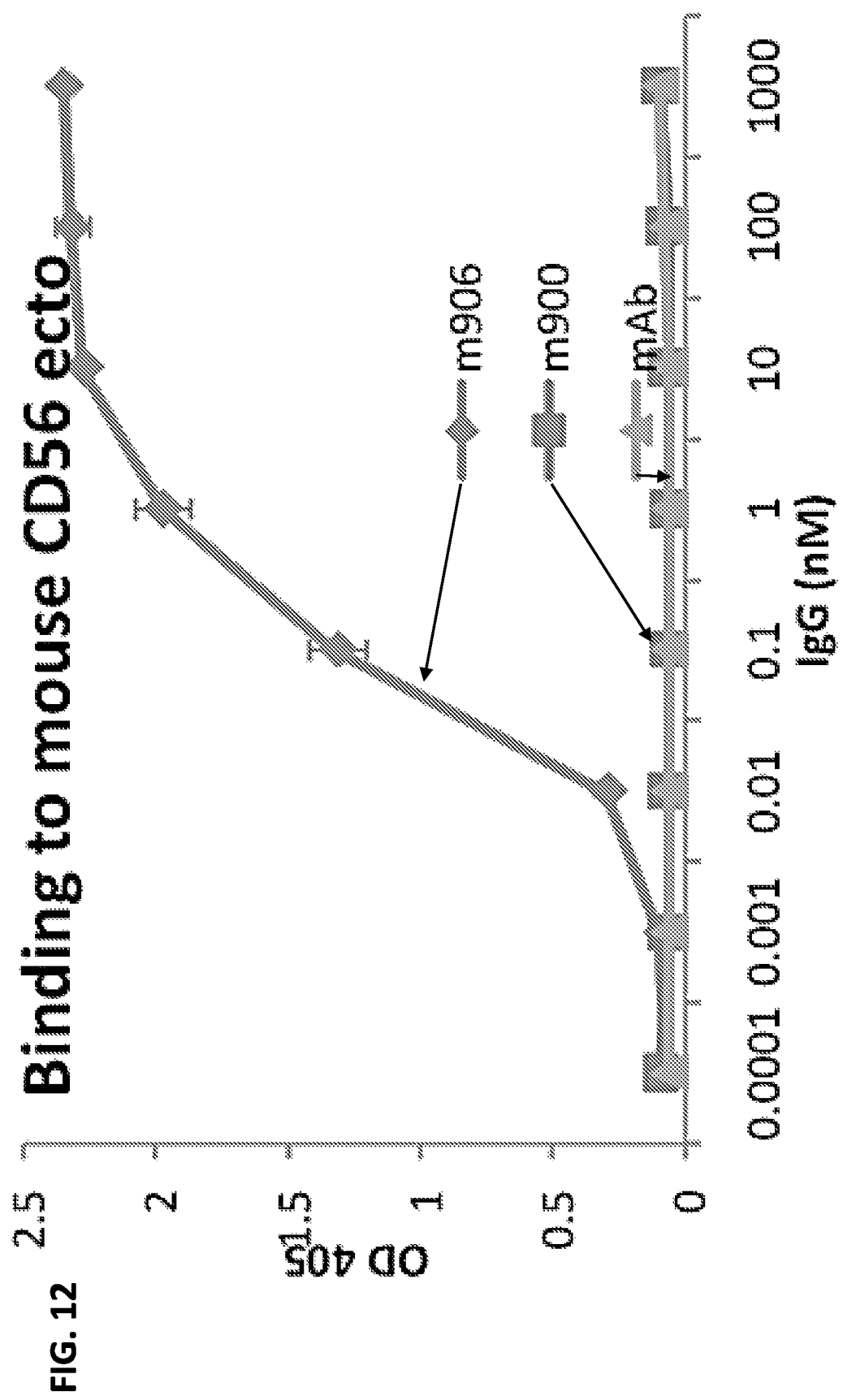
FIG. 12 is a graph showing antibody binding to mouse CD56 by ELISA. Antibody m906 binds mouse CD56, while m900 and a control anti-human CD56 antibody (mAb) do not.

Fully human CD56 antibodies have not been previously reported. In this study, several CD56 antibodies were identified from a human naïve Fab phage library through library panning and screening. Two of the clones, named m900 and m906, are described in detail herein. m900 and m906 were found to bind to different regions of the CD56 molecule (FIG. 1A). As shown in FIG. 1B, while m900 bound to the membrane-proximal region on the two fibronectin III domains, m906 bound to the N terminal IgG-like domains. The two antibodies do not compete for binding to CD56 on ELISA. By BIACORE™ analysis, the two antibodies had similar binding affinity to CD56. In the Fab format, the two antibodies have nanomolar dissociation rate constants (m900: $K_D$=2.9 nM and m906: $K_D$=4.5 nM). An ELISA was also performed to test binding of m900 and m906 to mouse CD56. As shown in FIG. 12, m906, but not m900, bound mouse CD56. A commercial mouse anti-human CD56 antibody (BD Bioscience; cat #555514) was used as a negative control in this experiment.

It has been reported that the five IgG-like domains and the two fibronectin type III-like domains of CD56 protein have different functions. The N-terminal IgG liked domains are thought to be involved in cell-cell adhesion through homophilic interaction with IgG-like domains of CD56 on another cell/matrix or on the same cell. The fibronectin type III domain might be involved in downstream signaling. Given the functional difference of the domains, it was investigated whether the two antibodies have different binding behavior on neuroblastoma cells, which are CD56 positive.

Surface Levels and the Dynamic of CD56 in Neuroblastoma Cell Lines

Figures 2A, 2B:
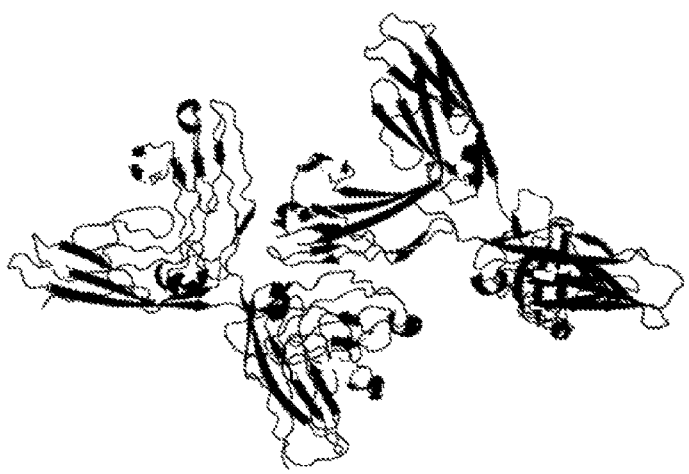
FIG. 2A is a table listing the affinity of m900 and m906 for the CD56 ectodomain, as measured by BIACORE™ analysis.
FIG. 2B shows a molecular model of m900 and m906 bound to mouse CD56.
Figure 5:
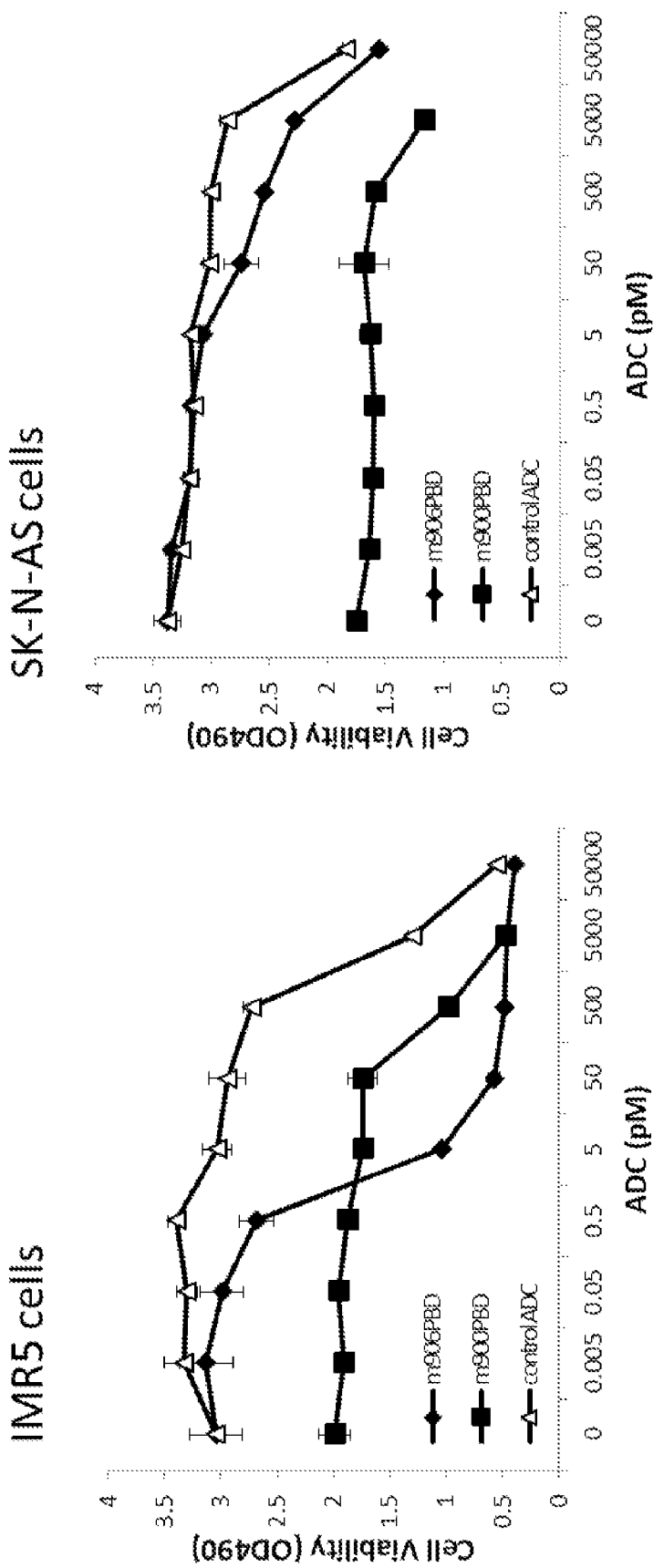
FIG. 5 is a pair of graphs demonstrating that m906PBD kills IMR5 cells efficiently after a 4-day incubation. IMR5 (left) and SK-N-AS (right) cells were treated with m900PBD, m906PBD or a control ADC at concentrations 0.005, 0.05, 0.5, 5, 50, 500, 5000, or 50,000 pM for 4 days. The cell viability was measured at OD490 after a substrate was added. Each concentration was tested in triplicate wells.

Two neuroblastoma cell lines, IMR5 and SK-N-AS, were used to characterize the CD56-binding ability of the antibodies. First, CD56 surface levels were measured with a mouse monoclonal antibody using flow cytometry. As shown in FIG. 2, IMR5 cells have higher levels of CD56 than SK-N-AS. IMR5 is a subclone of the IMR32 cell line isolated from a 5-year-old patient. It is a fast growing neuroblast cell line with fibroblast-like morphology. SK-N-AS is neuroblast cell line with epithelial-like morphology. Features of the two cell lines are listed in Table 1. When measured with a mouse anti-human CD56 monoclonal antibody (BD Biosciences) on flow cytometry, IMR5 cells had higher levels of surface CD56 than the SK-N-AS cells. Binding of the antibodies m900 and m906 have a similar pattern.

TABLE 1

Features of the IMR5 and SK-N-AS neuroblastoma cell lines

|  | IMR5 | SK-N-AS |
| --- | --- | --- |
| Tumor primary site | abdomen | brain |
| Tumor metastatic site | abdomen | bone marrow |
| Cell type | neuroblast | neuroblast |
| Cell morphology | neuroblast | epithelial |
| CD56 surface level | medium | low |

Many cell surface receptors, such IGF-1R, undergo down-regulation upon binding of their cognate ligands or antibodies. The possibility of CD56 down-regulation was tested using two methods. First, a comparison was carried out of when m900 or m906 were incubated with the two cell lines at 37° C. versus 4° C. for 1 hour during the primary antibody incubation step for flow cytometry. It was found that incubation of m906 with either cell line at 37° C. gave lower binding signal than incubation at 4° C., indicating m906 incubation at 37° C. might have led to internalization of CD56. This reduction was not detected when m900 was tested. In a more elaborate experiment, IMR5 and SK-N-AS cells were treated with m900 or m906 IgG overnight, cells were then detached with Cell Dissociation Buffer and stained with the mouse anti-human CD56 antibody to measure the surface levels of CD56 that still remained. It was found that overnight incubation of m906 had clearly caused the reduction of surface CD56 in IMR5 and SK-N-AS cells, with IMR5 having a greater reduction than the SK-N-AS cells. In either cell line, m900 did not reduce the surface levels of CD56 significantly. These results indicate that antibody binding to the distal IgG-like domains induced down-regulation of CD56 in these two neuroblastoma cell lines.

Some receptors or surface proteins (such as many G protein-coupled receptors) are quickly recycled back to the cell surface after they are internalized, whereas some receptors are internalized deeply into lysosomes of cells, whereupon the protein is proteolytic ally degraded. The difference in the depth of internalization has implications when the binding antibody is considered as a therapeutic. For example, antibody-drug conjugates rely on the release of drugs at the lysosome to make the cytotoxic drugs available. It was therefore tested whether m906-induced internalization of CD56 goes inside cells as deep as lysosomes. This was performed by utilizing a commercial reagent hFab-ZAP. hFab-ZAP is an Fab fragment that recognizes human Fc, and is coupled with saporin, a very potent ribosomal-inactivating protein (Kohls, *Biotechniques* 28(1):162-165, 2000). When hFab-ZAP gains entry to cells through the primary antibody, in this case m900 or m906, and is released from the lysosomes, it inhibits protein synthesis and induces apoptosis.

IMR5 and SK-N-AS cells were incubated with fixed concentrations of hFab-ZAP in combination with a range of m900 and m906. After two days incubation, the cell viability was monitored. The results showed that m906 and hFab-ZAP co-incubation in both IMR5 and SK-N-AS cells caused cell death in an m906 dose dependent-fashion. Co-incubation of m900 with hFab-ZAP did not cause significant cell death. These results indicate that m906-induced internalization of CD56 did go through the lysosome pathway, and thus is a candidate for designing antibody-drug conjugates. In addition, the internalization result in IMR5 cells and SK-N-AS cells agree with the results observed in the CD56 down-regulation experiment.

CD56 Antibody-drug Conjugate m906 Induced Cell Death in CD56-positive Neuroblastoma Cell Line IMR5

Because m906 is a high affinity fully human antibody with the ability to induce CD56 internalization, it is a good candidate for developing antibody-drug conjugates. m906 was conjugated with PBD (pyrrolobenzodiazepines dimers) through the internal cysteines. PBD is a relatively new highly cytotoxic small molecular drug. PBD cross-links DNA by binding to the minor groove and causes DNA damage, which leads to apoptosis. m900PBD was also tested even though m900 did not induce CD56 internalization. As a negative control, m610, a human monoclonal antibody to IGF2, was also conjugated to PBD. IMR5 and SK-N-AS cells were treated with all three ADCs and the results indicated that m906PBD had potent killing effect on IMR5 cells, and less so on SK-N-AS cells. In IMR5 cells, the IC50 of m906PBD was several pM, whereas the control ADC only showed some toxicity at 5000 pM. This difference gave a large therapeutic window. m900PBD caused some cell death at >500 pM, in agreement with its inefficient internalization. In SK-N-AS cells, m906PBD was not very potent, despite the internalization by m906. This might be due to the overall low levels of CD56 on surface plus low internalization rate in SK-N-AS cells, so that the PBD drug did not reach the critical concentration inside cells.

CD56 Positive Neuroblastoma Cells SK-N-AS are Subject to ADCC Mediated by CD56 Antibodies Antibodies such as IgG1s have inherent effector functions through their Fc interaction with Fcγ receptors on natural killer cells (ADCC for antibody-dependent cell-mediated cytotoxicity) or through complement-dependent cytotoxicity (CDC). ADCC by natural killer cells requires binding of multiple copies of antibodies on the target cells, which confers the avidity effect to the low affinity receptor FcγIIIa (or CD16a) on the effector cells. However, ADCC does not require internalization of the target molecule. In fact, sustained presentation of the target molecule on the surface of the target cells should favor the ADCC process. The possible ADCC effect mediated by m906 and m900 was investigated. To enhance ADCC of the two antibodies, a de-fucosylated form of the antibodies was produced by including a fucosylation inhibitor during the production.

First, an engineered Jurkat cell line with stable expression of human CD16a was used as the source of effector cells. The established stable cell line provided an endless source of effector cells, and were thus convenient for the initial test. These Jurkat cells also carry NFAT (a downstream signal molecule after CD16a) and the luciferase gene as the reporter. An increase in luciferase indicates interaction of CD16a on Jurkat cell with the Fc of bound IgG1s on the target cells. A generally low level of luciferase activity was detected in IMR5 cells, although m900-induced activity was slightly higher than the rest of the samples. Most significantly, de-fucosylated m900 induced high reporter gene activity in SK-N-AS cells, indicating the interaction of CD16a with defucosylated Fc of m900.

Second, PBMCs isolated from healthy donors were used as the effector cells. Using these cells allowed observing actual lysis of the target cells. Co-incubation of IMR5 cells with antibodies and PBMCs gave low percentage of cell lysis, although de-fucosylated m900 at higher concentration showed a positive reaction. As was observed in the first ADCC method, in SK-N-AS cells, defucosylated m900 had marked increase in the lysis of the target cells.

Therapeutic Applications

CD56 is an important cancer target in many tumors, including neuroblastoma, multiple myeloma, small cell lung cancer, acute myeloid leukemia, Wilms tumor and ovarian cancer. Antibody-guided target therapy for these diseases will be a welcome addition to the available treatment choices. In the literature, the reported CD56 antibody-drug conjugate, IMGN901, has a humanized CD56 antibody. It has been reported that IMGN901 showed clinical efficacy in small cell lung cancer. IMGN901 had a short half-life of 18-24 hours in humans (similar to its plain antibody), which may be attributed to the uptake of CD56 in some normal tissues. However, a fully human CD56 antibody may have a longer half-life. Disclosed herein is the identification and characterization of two CD56 human antibodies. These antibodies can be used as naked antibodies or as drug conjugates for treatment of CD56-positive cancers.

Example 3: Preparation and Characterization of m906-Z-PBD ADC

This example describes the generation and cell killing properties of a CD56-specific ADC (m906-Z-PBD) prepared using glycan engineering.

Figure 8:
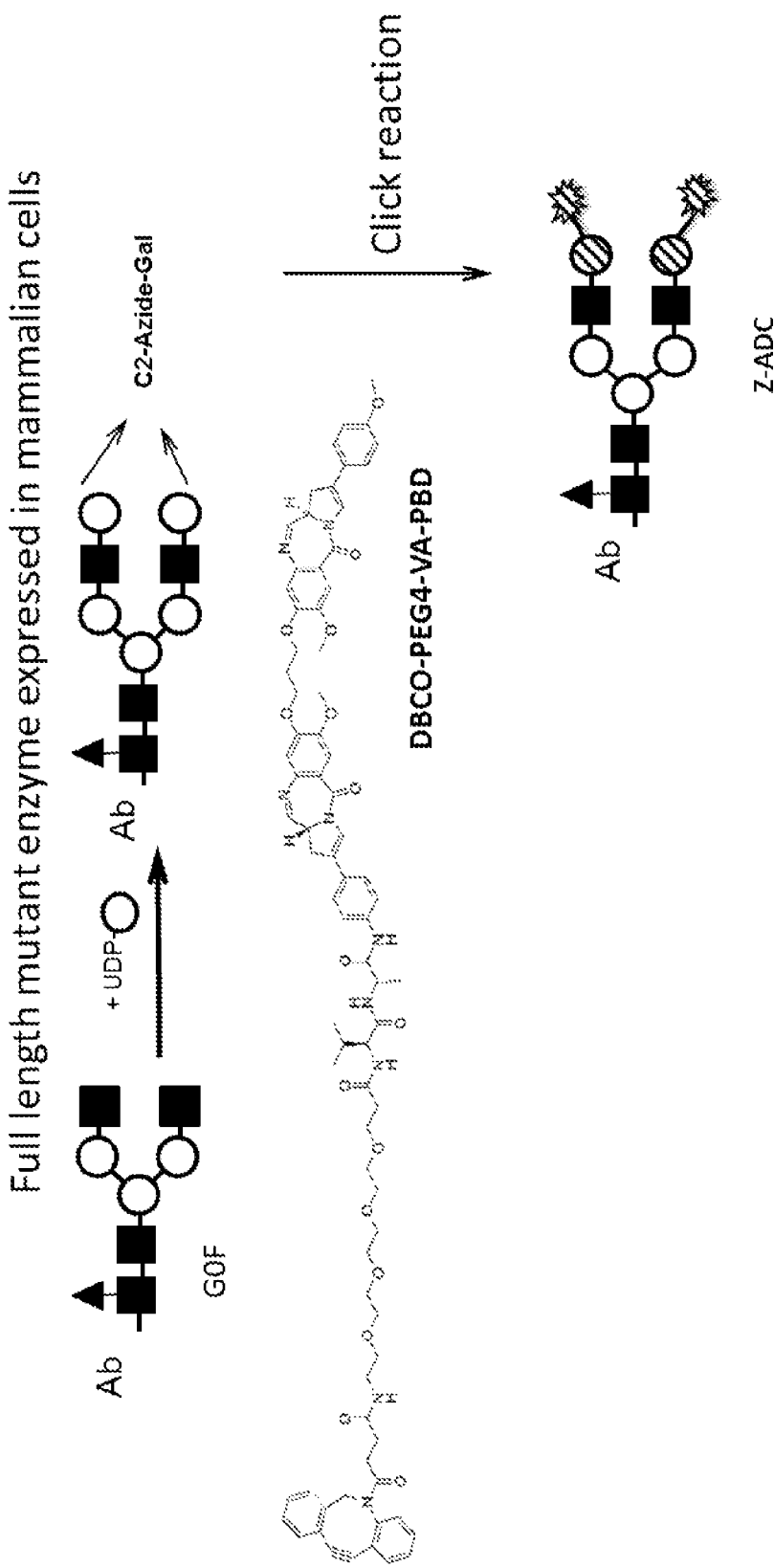
FIG. 8 depicts the conjugation method used to produce the m906-Z-PBD ADC. The drug DBCO-PEG4-PBD was conjugated to the m906 antibody carbohydrates via Click reaction. The molar ratio of antibody to drug was 2:1.

The m906-Z-PBD ADC was prepared by conjugating the drug DBCO-PEG4-PBD to m906 antibody carbohydrates via a Click reaction (see FIG. 8). The drug to antibody ratio used was 2:1 (molar ratio). A UV reading at 330 nm confirmed conjugation of PBD to the antibody. The antibody maintained monomer status before and after conjugation.

Figure 9:
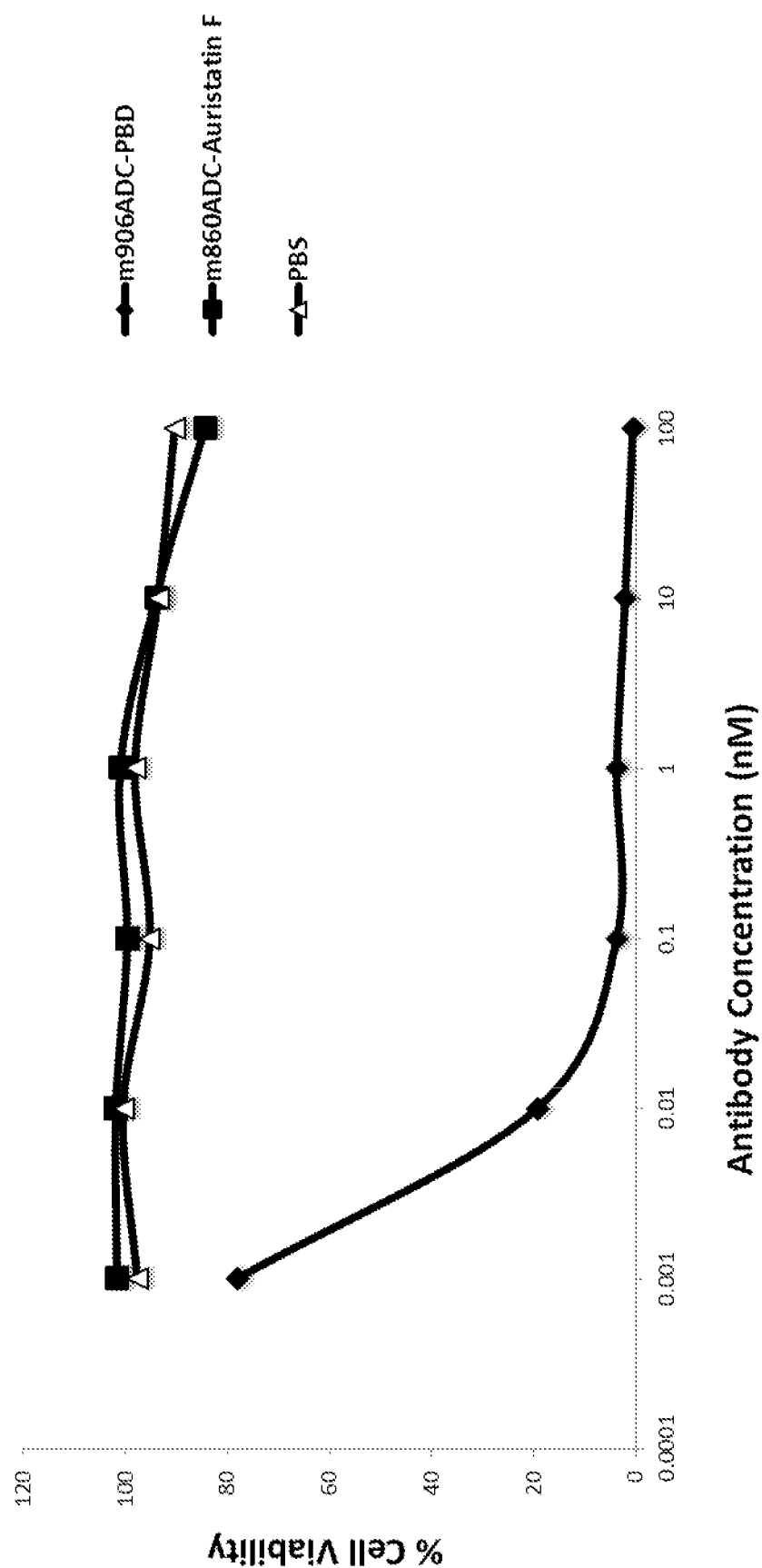
FIG. 9 is a graph showing cell killing activity of m906-Z-PBD on IMR5 cells (CD56$^+$, Her2$^-$). m906-Z-PBD potently killed IMR5 cells, while an ADC that binds Her2 (m860ADC-Auristatin F) had no effect on viability of the IMR5 cells.
Figure 10:
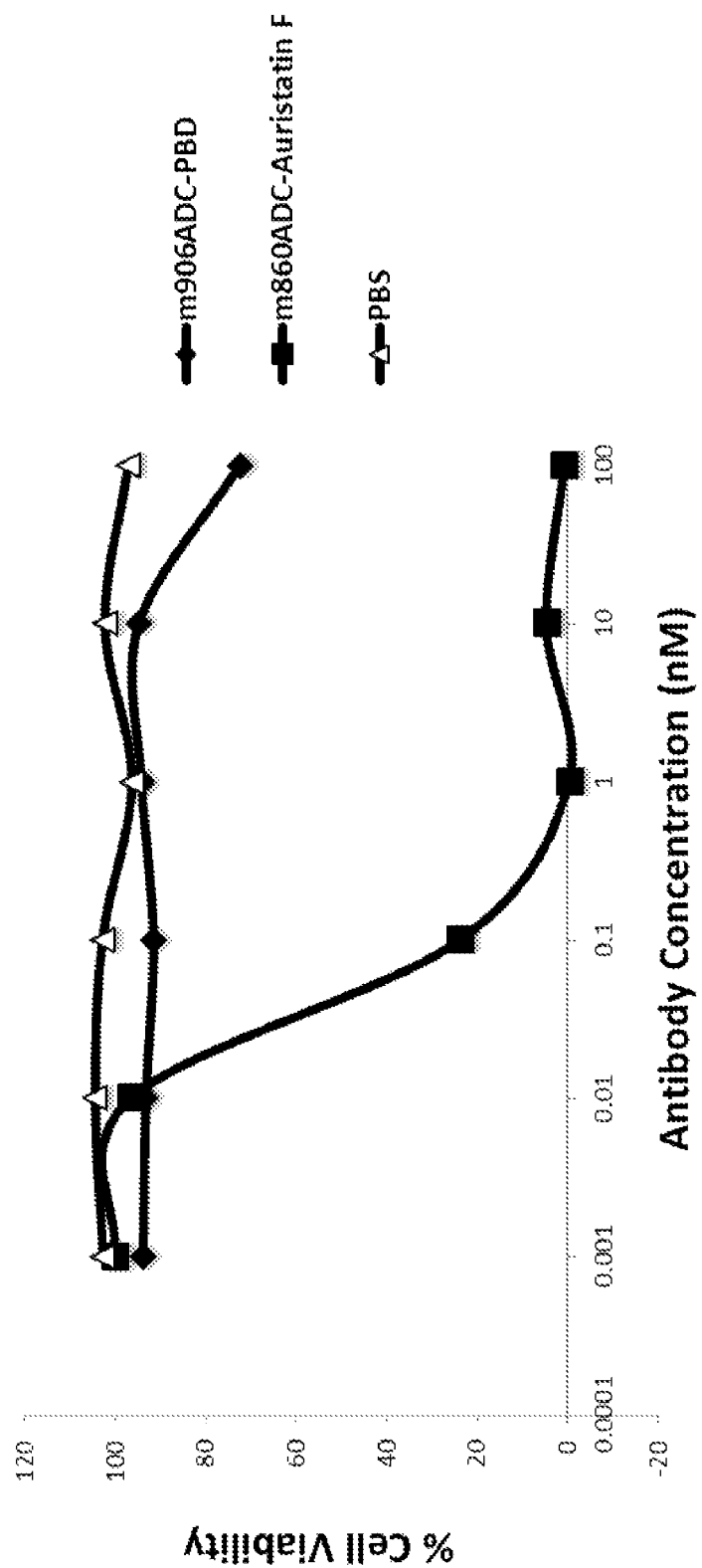
FIG. 10 is a graph showing cell killing activity of m906-Z-PBD on SKRB3 cells (CD56$^-$, Her2$^+$). m906-Z-PBD did not significantly affect viability of the CD56-negative SKRB3 cells. In contrast, the Her2-specific ADC m860ADC-Auristatin F was cytotoxic to SKRB3 cells.

Cell killing of the m906-Z-PBD ADC was tested on both CD56-positive IMR5 cells and CD56-negative SKRB3 cells. An ADC that binds Her2 (m860ADC-Auristatin F) was used as a control in these experiments. m860ADC-Auristatin F and m906-Z-PBD were conjugated using the same linker chemistry. As shown in FIG. 9, m906-Z-PBD potently killed IMR5 cells, while m860ADC-Auristatin F had no effect on viability of the IMR5 cells, which are Her2-negative. In contrast, the m906-Z-PBD ADC did not significantly affect viability of the CD56-negative SKRB3 cells, while m860ADC-Auristatin F was cytotoxic to SKRB3 cells, which are Her2-positive (FIG. 10).

Figure 11:
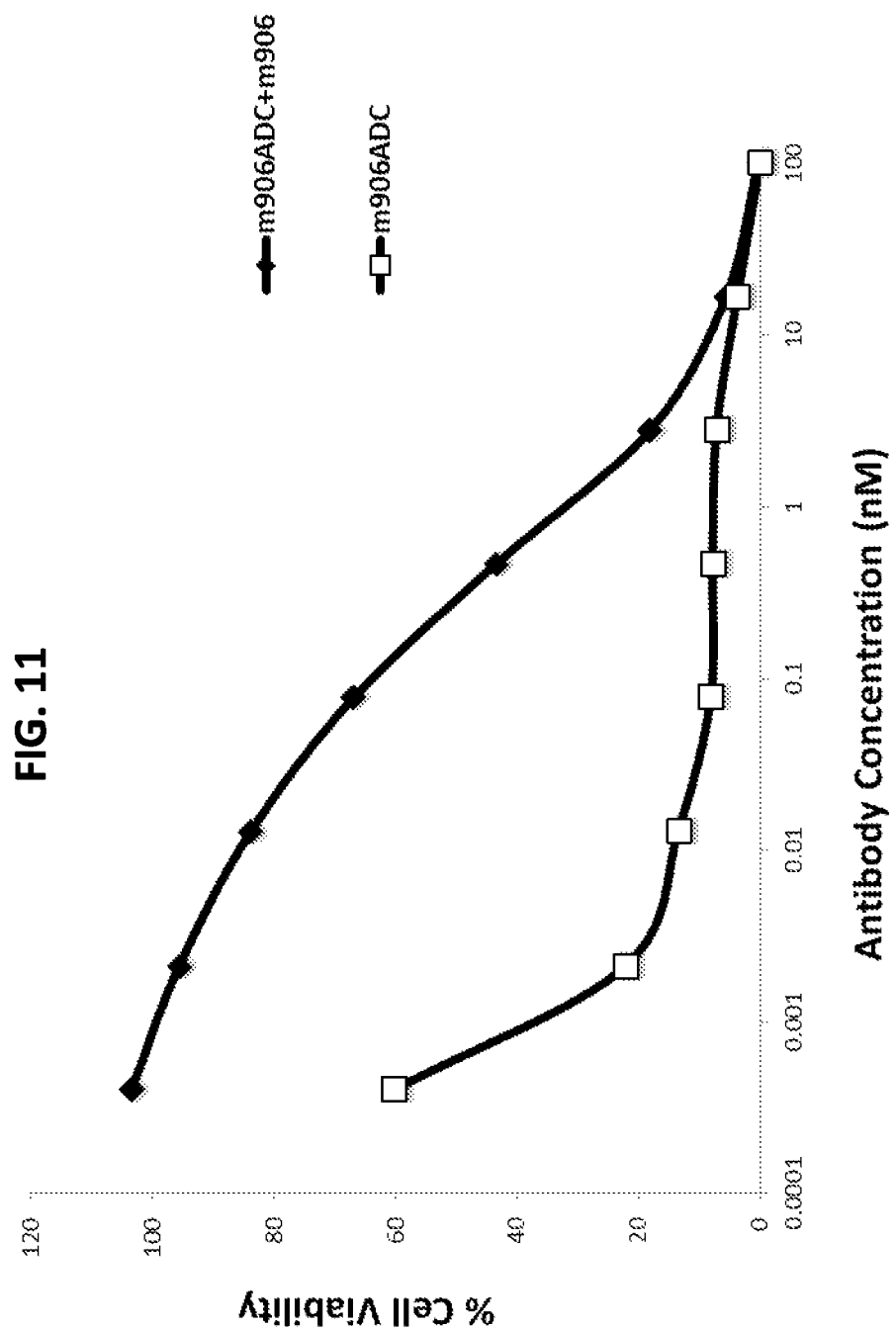
FIG. 11 is a graph showing inhibition of m906-Z-PBD-induced cell killing by m906 IgG. Shown in the graph is percent cell viability of IMR5 cells treated with m906-Z-PBD alone (m906ADC) or with the combination of m906-Z-PBD and m906 IgG (m906ADC+m906). The m906 IgG was able to compete for CD56 binding, thereby inhibiting cell killing by the ADC.

Next, the ability of unconjugated m906 to compete with m906-Z-PBD was tested. FIG. 11 shows the percent cell viability of IMR5 cells treated with m906-Z-PBD alone (m906ADC) or with the combination of m906-Z-PBD and m906 IgG (m906ADC+m906). The results demonstrate that m906 IgG is able to compete for CD56 binding, thereby inhibiting cell killing by the ADC.

Example 4: m906-PBD Prolongs Tumor Regression and Increases Survival in an Animal Model of Neuroblastoma The results described in this example demonstrate that the antibody m906 induces internalization of CD56 on CD56-expressing cells, and that an ADC comprised of m906 kills CD56-positive cells in vitro, and induces prolonged tumor regression and increases survival in an in vivo model of CD56-positive neuroblastoma.

To evaluate whether m906 can induce internalization of cell-surface CD56, the neuroblastoma cell lines SKNFI, Kelly and NB16 were stained using m906IgG. Cells were treated for 48 hours (SKNFI and Kelly cells) or 72 hours (NB16 cells) with 50 nM m906IgG and then stained using anti-human IgG secondary antibody to detect m906IgG-CD56 complex localization. Lamp1 detection was used as a lysosomal marker. The results demonstrated that following treatment with m906IgG, CD56 was internalized to the lysosomes.

Figure 13A:
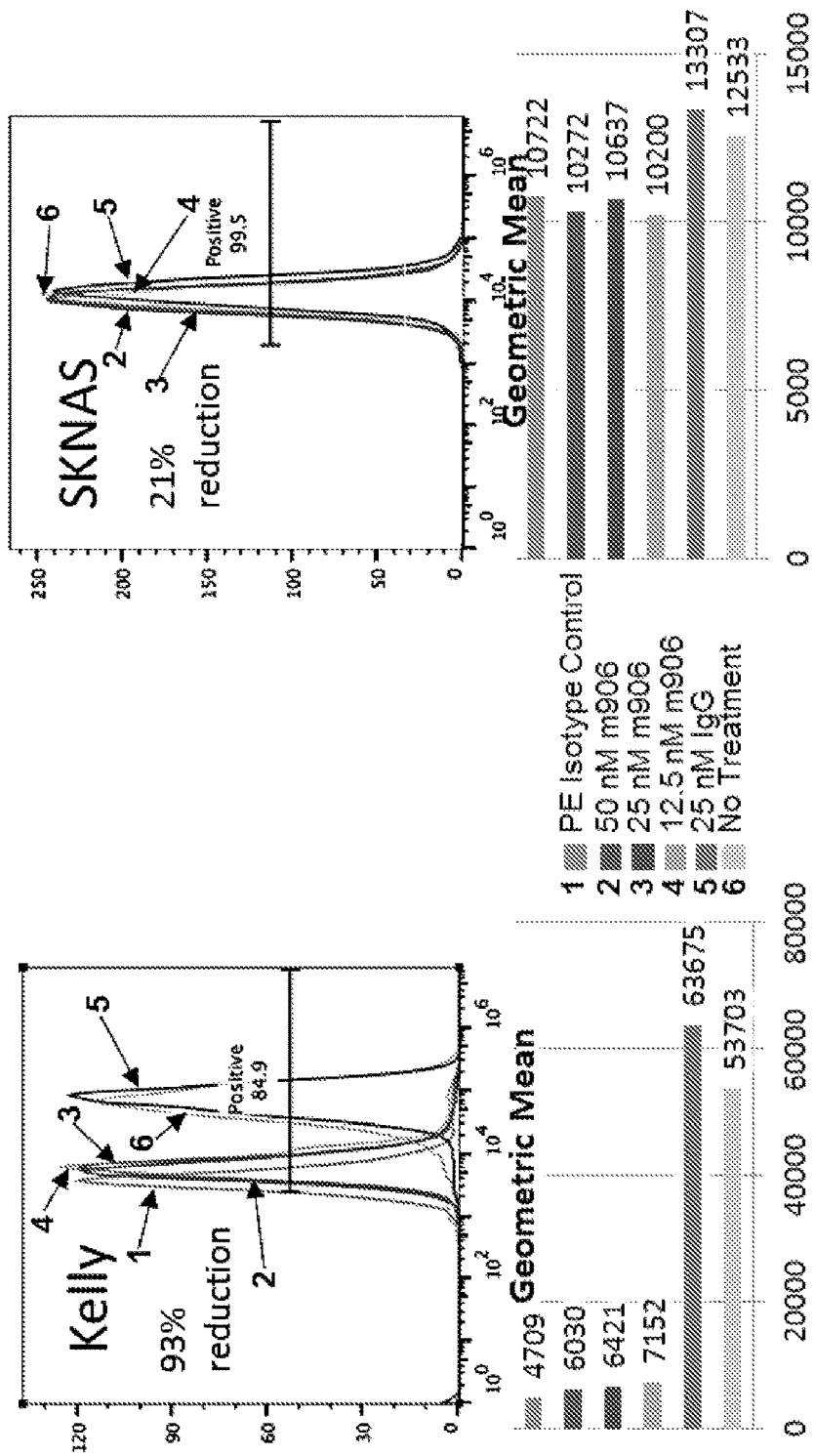
FIGS. 13A-13B show quantification of m906 internalization.
Figure 13B:
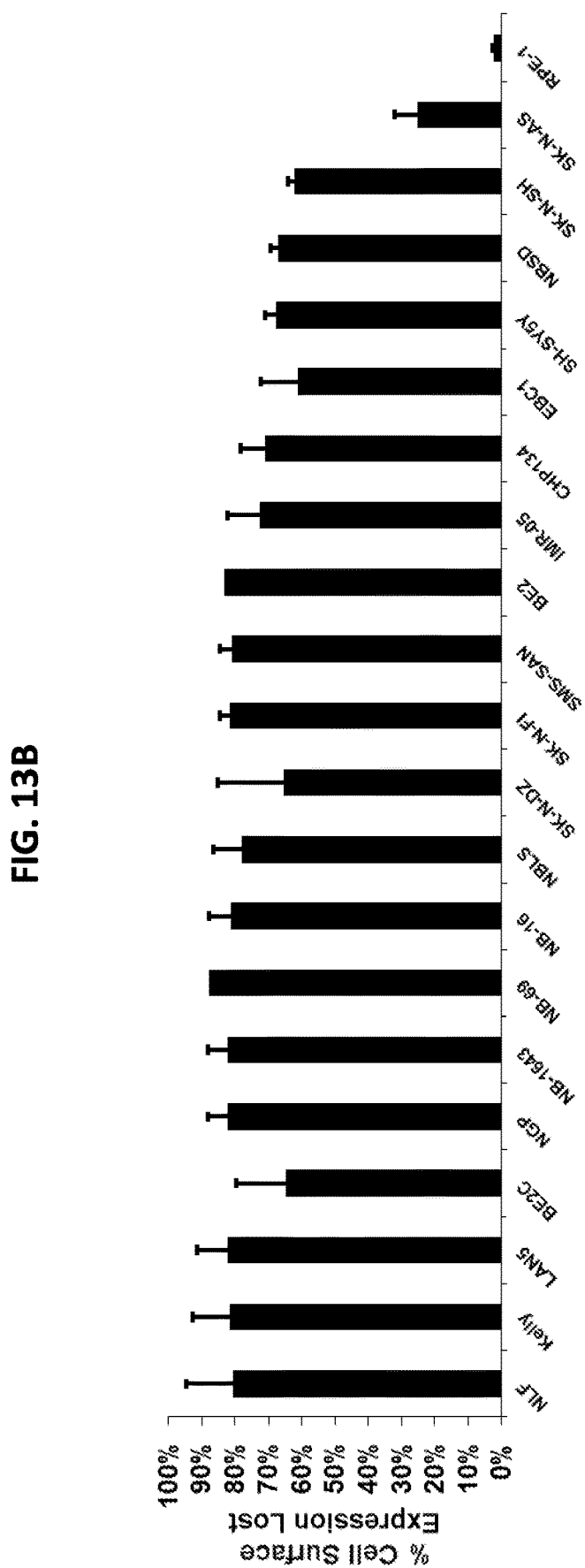

Another study was performed to quantify m906 internalization. Kelly cells and SKNAS cells were either untreated or treated overnight with 25 nM control IgG, 12.5 nM m906, 25 nM m906 or 50 nM m906 and the remaining cell surface expression of CD56 was detected using anti-CD56 antibody MY31. The results demonstrated that untreated and control IgG-treated Kelly cells expressed CD56 on the surface, and this expression was reduced by approximately 93% in cells pre-treated with m906 (FIG. 13A, left). The percent reduction in cell surface expression was calculated using the 50 nM m906 treatment and no treatment groups (1−(m906/no treatment)). SKNAS cells expressed very little CD56 and showed little difference (21% reduction) in CD56 cell surface expression when pre-treated with m906 (FIG. 13A, right). Several other neuroblastoma cell lines were similarly tested by overnight pre-treatment with 50 nM m906. The percent reduction in CD56 cell-surface expression in each cell line resulting from m906 pre-treatment is shown in FIG. 13B. All neuroblastoma cells lines (other than SKNAS cells) exhibited a reduction of at least 60% following treatment with m906.

M906 was conjugated to PBD to form a CD56-specific ADC. To test cell killing of m906-PBD, an in vitro cell death assay was performed. Seventeen neuroblastoma cell lines were treated with limiting dilutions of m906-PBD for 96 hours. The dose response curves are shown in FIG. 14. IC50 concentrations for each cell line were in the picomolar range.

Figure 15:
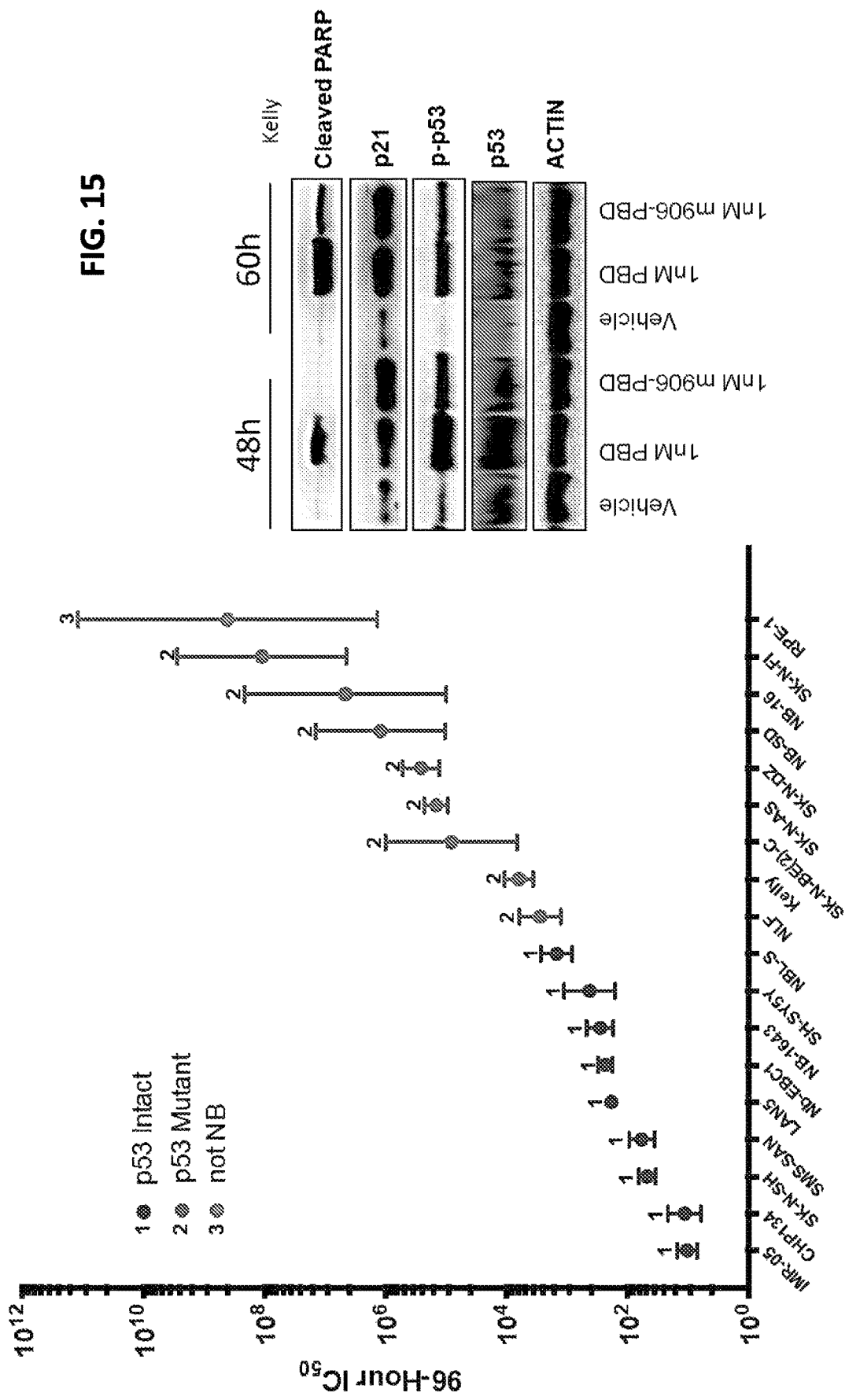
FIG. 15 shows that p53 status determines sensitivity to m906-PBD. Sensitivity to m906-PBD did not correlate to cell surface expression of CD56 or ability to internalize the m906-CD56 complex. However, as shown in the graph on the left, m906-PBD induced greater cell killing of neuroblastoma cell lines with mutant p53, compared to cells with intact p53. Kelly cells have partially functional p53 and the western blot (right) shows that at 48 hours, both free PBD and m906-PBD cause phosphorylation of p53 and induction of P21. PARP cleavage was observed with free PBD treatment after 48 hours and with m906-PBD treatment after 60 hours.

Sensitivity to m906-PBD did not correlate with cell-surface expression of CD56 or the ability to internalize the m906-CD56 complex. Therefore, a study was performed to determine whether p53 status determines sensitivity to m906-PBD. As shown in FIG. 15 (left) sensitivity to m906-PBD correlated with p53 functionality; neuroblastoma cells with intact p53 were more sensitive to cell killing by m906-PBD, compared to cell lines with mutant p53. Kelly cells have partially functional p53. As shown by western blot (FIG. 15, right), at 48 hours, free PBD or m906-PBD caused phosphorylation of p53 and induction of P21. PARP cleavage was observed with free PBD treatment after 48 hours and with m906-PBD treatment after 60 hours.

Another experiment was conducted to determine whether m906 antibody is capable of blocking the cytotoxic effect of m906-PBD. FIG. 16 shows the results of an antibody competition assay. CHP134 cells were treated with limiting dilutions of m906-PBD or free PBD. M906 was used to compete off m906-PBD at 25×, 50× and 100× the m906-PBD dose. M906 was able to prevent cell death in a dose-dependent manner.

Figure 17A:
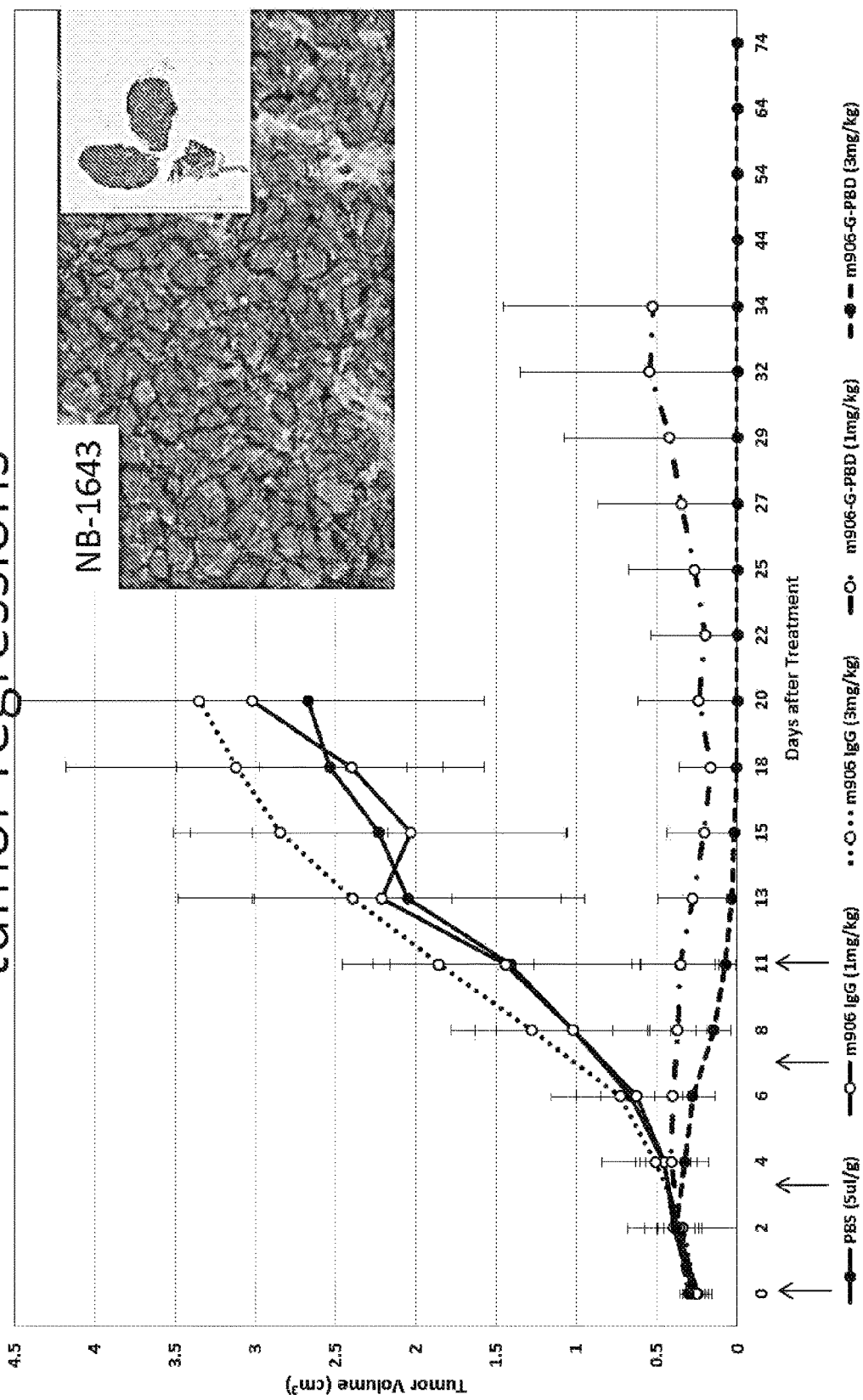
FIGS. 17A-17B are graphs showing the results in vivo treatment with m906-PBD. CB17 SCID mice bearing 0.2 cm$^3$ NB1643 patient derived xenograft tumors were treated with 1 or 3 mg/kg of m906 or m906-PBD by IP injection twice a week for two weeks, as indicated by the arrows.
Figure 17B:
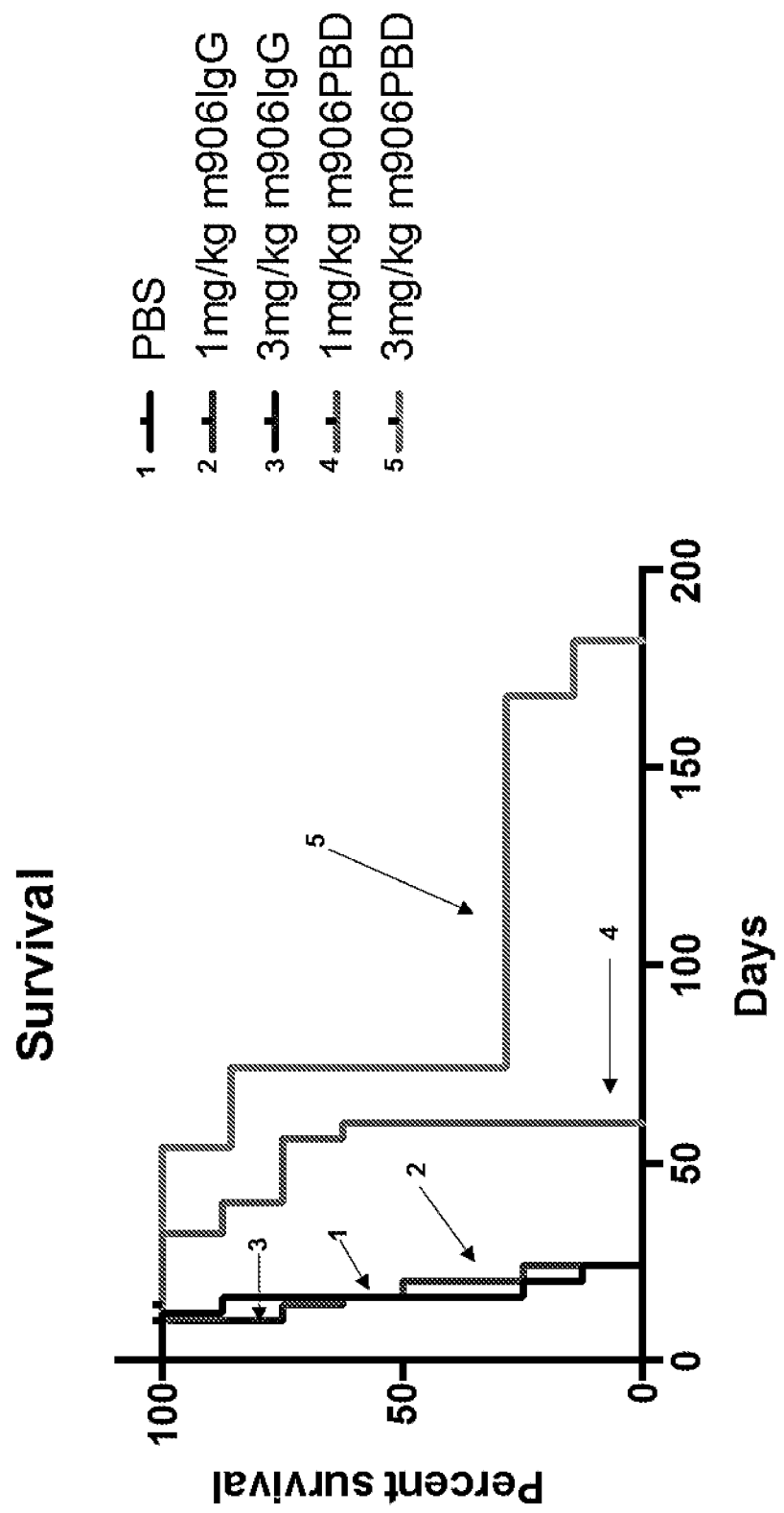

Next, m906-PBD was tested in an animal model of neuroblastoma. CB17 SCID mice bearing 0.2 cm$^3$ NB1643 patient derived xenograft tumors were treated with 1 or 3 mg/kg of m906 or m906-PBD by intraperitoneal injection twice a week for two weeks. As shown in FIG. 17A, treatment with m906-PBD induced prolonged tumor regression. In particular, two mice treated with 3 mg/kg m906-PBD exhibited no detectable disease for over 150 days post enrollment. Treatment with m906-PBD, particularly at a dose of 3 mg/kg, also led to increased survival of mice bearing xenograft tumors, as shown in FIG. 17B.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. An antibody-drug conjugate (ADC), comprising a drug conjugated to a CD56-specific monoclonal antibody, or an antigen-binding fragment thereof, wherein the monoclonal antibody or antigen-binding fragment thereof comprises a variable heavy (VH) domain and a variable light (VL) domain, and wherein:

the VH domain comprises the complementarity determining region (CDR) sequences of SEQ ID NO: 6 and the VL domain comprises the CDR sequences of SEQ ID NO: 8.

2. The ADC of claim 1, wherein the CDR sequences are CDR sequences determined by IMGT or by Kabat.

3. The ADC of claim 2, wherein:

the VH domain comprises amino acid residues 26-33, 51-59 and 97-111 of SEQ ID NO: 6 and the VL domain comprises amino acid residues 27-37, 55-57 and 94-103 of SEQ ID NO: 8.

4. The ADC of claim 2, wherein:

the VH domain comprises amino acid residues 31-35, 50-66 and 99-110 of SEQ ID NO: 6 and the VL domain comprises amino acid residues 24-39, 55-61 and 94-102 of SEQ ID NO: 8.

5. The ADC of claim 1, wherein the VH domain comprises an amino acid sequence at least 90% identical to SEQ ID NO: 6 and the VL domain comprises an amino acid sequence at least 90% identical to SEQ ID NO: 8.

6. The ADC of claim 5, wherein the VH domain comprises the acid sequence of SEQ ID NO: 6 and the VL domain comprises the amino acid sequence of SEQ ID NO: 8.

7. The ADC of claim 1, wherein the drug comprises a cytotoxic agent.

8. The ADC of claim 7, wherein the cytotoxic agent comprises an interstrand crosslinking agent, an anti-mitotic agent or an anti-microtubule agent.

9. The ADC of claim 8, wherein the interstrand crosslinking agent comprises a pyrrolobenzodiazepine (PBD).

10. The ADC of claim 1, wherein the antigen-binding fragment is an Fab fragment, an Fab' fragment, an F(ab)'$_2$ fragment, a single chain variable fragment (scFv) or a disulfide stabilized variable fragment (dsFv).

11. The ADC of claim 1, wherein the monoclonal antibody is an IgG.

12. The ADC of claim 1, wherein the monoclonal antibody, or antigen-binding fragment thereof, is a fully human antibody.

13. The ADC of claim 1, wherein the monoclonal antibody, or antigen-binding fragment thereof, is chimeric or synthetic.

14. A composition comprising the ADC of claim 1 and a pharmaceutically acceptable carrier.

15. A method of treating a subject having a CD56-positive cancer, comprising selecting a subject with a CD56-positive cancer and administering to the subject a therapeutically effective amount of the ADC of claim 1, wherein the CD56-positive cancer is a neuroblastoma, multiple myeloma, ovarian cancer, acute myeloid leukemia, Wilms tumor or small cell lung cancer.

16. A method of inhibiting tumor growth or metastasis of a CD56-positive cancer in a subject, comprising selecting a subject with a CD56-positive cancer and administering to the subject a therapeutically effective amount of the ADC of claim 1, wherein the CD56-positive cancer is a neuroblastoma, multiple myeloma, ovarian cancer, acute myeloid leukemia, Wilms tumor or small cell lung cancer.

* * * * *